US006448062B1

(12) United States Patent
Huth et al.

(10) Patent No.: US 6,448,062 B1
(45) Date of Patent: Sep. 10, 2002

(54) SIMULTANEOUS CLEANING AND DECONTAMINATING COMPOSITIONS AND METHODS

(75) Inventors: Stanley William Huth, Newport Beach; Zhi-Jian Yu, Irvine, both of CA (US)

(73) Assignee: Metrex Research Corporation, Orange, CA (US)

( * ) Notice: Subject to any disclaimer, the term of this patent is extended or adjusted under 35 U.S.C. 154(b) by 0 days.

(21) Appl. No.: 09/430,398

(22) Filed: Oct. 29, 1999

Related U.S. Application Data

(63) Continuation-in-part of application No. 09/183,186, filed on Oct. 30, 1998, now abandoned.

(51) Int. Cl.[7] ............................................. D06M 16/00

(52) U.S. Cl. ..................... 435/264; 510/109; 510/114; 510/161; 510/162; 510/374; 510/375; 510/382; 510/392

(58) Field of Search ................................ 510/161, 162, 510/382, 108, 109, 114, 363, 367, 374, 375, 392, 401; 435/264; 134/42

(56) References Cited

U.S. PATENT DOCUMENTS

| 3,714,050 A | 1/1973 | Gray ........................... 252/99 |
| 3,816,319 A | 6/1974 | Sarot et al. .................... 252/95 |
| 3,912,451 A | 10/1975 | Gaglia, Jr. ...................... 21/58 |
| 4,690,772 A | 9/1987 | Tell et al. ..................... 252/106 |
| 4,731,222 A | 3/1988 | Kralovic et al. ............... 422/37 |

(List continued on next page.)

FOREIGN PATENT DOCUMENTS

| CA | 1273774 | 9/1990 |
| CA | 1320030 | 7/1993 |
| CA | 1321137 | 8/1993 |
| DE | 2 130 833 | 1/1973 |
| EP | 0 219 220 | 4/1987 |
| EP | 0 232 170 | 8/1987 |
| EP | 0 307 376 A1 | 3/1989 |
| EP | 0 342 499 | 5/1989 |
| EP | 0 322 310 | 6/1989 |
| EP | 0 397 352 | 11/1990 |
| EP | 0 722 740 A2 | 7/1996 |
| GB | 2 129 458 A | 5/1984 |
| WO | 91/16423 | 10/1991 |
| WO | WO 97/42825 | 11/1997 |
| WO | WO 98/11777 | 3/1998 |

OTHER PUBLICATIONS

M. Best; VS Springthorpe; SA Sattar, *Feasibility of a Combined Carrier Test for Disinfactant: Studies With a Mixture of Five Types of Microorganisms*, Am J Infect Control; Jun. 1994, 22:3, 152–62.

Martin et al., *APIC Guideline for Infection Prevention and Control in Flexible Endoscopy*, Am J Infect Control, 22:19–38 (1994).

Maisonneuve et al., *Cancer in patients on dialysis for end-stage renal disease: an international collaborative study*, The Lancet, 354, 93–99 (1999).

Buettner et al., *Catalytic Metals, Ascorbate and Free Radicals: Combinations to Avoid*, Radiation Research 145, 532–541 (1996).

Melichercikova, V., *Desinfectant Effect of Persteril in Combination with Detergents*, Journal of Hygiene, Epidemiology, Microbiology and Immunology, 33, No. 1, pp. 19–28 (1989).

Kaplan et al., *Dialysate Protein Losses with Bleach Processed Polysulphone Dialyzers*, Kidney International, vol. 47, 573–578 (1995).

Keay et al., *Differentiation of Alkalilne Proteases from Bacillus Species*, Biochemical and Biophysical Research Communications, vol. 34, No. 5, 600–604 (1969).

Rutala et al., *Disinfection Practices for Endoscopes and Other Semicritical Items*, Infection Control Hospital Epidemiol, 12:282–8 (1991).

Murthy et al., *Effect of Formaldehyde/Bleach Reprocessing on In Vivo Performances of High–Efficiency Cellulose and High Flux Polysulfone Dialyzers*, J Am Soc Nephrol, 464–472 (1997).

Simmons, Bryan P., *Guideline for Hospital Environmental Control*, Am J Infect Control, 11:97–115 (1983).

Rutala, William A., *Guideline for Selection and Use of Disinfectants*, Am J Infect Control, Aug. 1996, vol. 24, 4:313–342.

Keay et al., *Proteases of the Genus Bacillus, Alkaline Proteases*, Biotechnology and Bioengineering, vol. XII, 213–249 (1970).

Perlmann, Gertrude E., *Proteolytic Enzymes*, Methods in Enzymology, vol. XIX, Acadenic Press, 642–650 (1970).

Pinkernell et al., *Simultaneous HPLC Determination of Peroxyacetic Acid and Hydrogen Peroxide*, Anal. Chem, 69, 3623–3627 (1997).

Alasri et al., *Sporocidal properties of peracetic acid and hydrogen peroxide, alone and in combination, in comparison with chlorine and formaldehyde for ultrafiltration membrane disinfection*, Can. J. Microbiol. vol. 39, pp. 52–60 (1993).

(List continued on next page.)

Primary Examiner—David A. Redding
(74) Attorney, Agent, or Firm—Wood, Herron & Evans, L.L.P.

(57) ABSTRACT

A composition for simultaneous cleaning and decontaminating a device. The composition is a per-compound oxidant in an amount effective for decontaminating the device and an enzyme in an amount effective for cleaning the device. The device may be a medical device such as an endoscope or kidney dialyzer and a plurality of devices can be cleaned using the same composition. The composition may additionally contain a corrosion inhibitor in an amount effective to prevent corrosion of a metal, a chelator, a buffer, a dye and combinations thereof.

4 Claims, 1 Drawing Sheet

U.S. PATENT DOCUMENTS

| | | | |
|---|---|---|---|
| RE32,672 E | 5/1988 | Huth et al. | 252/95 |
| 4,892,706 A | 1/1990 | Kralovic et al. | 422/28 |
| 5,037,623 A | 8/1991 | Schneider et al. | 422/292 |
| 5,077,008 A | 12/1991 | Kralovic et al. | 422/37 |
| 5,091,343 A | 2/1992 | Schneider et al. | 422/297 |
| 5,234,832 A | 8/1993 | Disch et al. | 435/264 |
| 5,269,959 A | 12/1993 | Schreibman | 252/100 |
| 5,323,442 A | 6/1994 | Golovanivsky et al. | 378/119 |
| 5,356,555 A | 10/1994 | Huth et al. | 252/106 |
| 5,364,554 A | 11/1994 | Stanislowski et al. | 252/186.38 |
| 5,376,387 A | 12/1994 | Monticello | 424/616 |
| 5,461,656 A | 10/1995 | Golovanivsky et al. | 378/66 |
| 5,480,565 A | 1/1996 | Levin et al. | 210/764 |
| 5,489,531 A | 2/1996 | Benson | 435/264 |
| 5,505,905 A | 4/1996 | Corby et al. | 422/102 |
| 5,552,112 A | 9/1996 | Schiffmann et al. | 422/21 |
| 5,571,488 A | 11/1996 | Beerstecher et al. | 422/297 |

OTHER PUBLICATIONS

M.G.C. Baldry Research and Development Department, *The Bactericidal, Fungicidal and Sporicidal Properties of Hydrogen Peroxide and Peracetic Acid*, Journal of Applied Bacteriology, 54, 417–423 (1983).

Buettner et al., *The Effect of Iron on the Distribution of Superoxide and Hydroxyl Radicals as Seen by Spin Trapping and on the Superoxide Dismutase Assay*, Photochemistry and Photobiology, vol. 28, 693–695 (1978).

Spach, David H., *Transmission of Infection by Gastrointestinal Endoscopy and Bronchoscopy*, An Intern Med, 118:117–28 (1993).

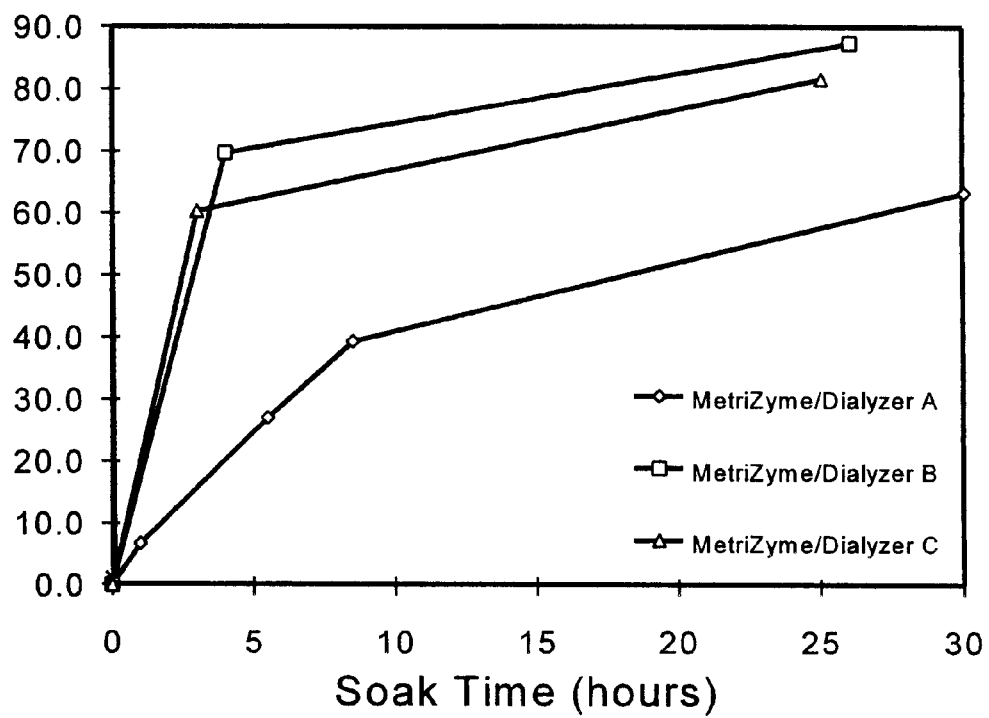

SIMULTANEOUS CLEANING AND DECONTAMINATING COMPOSITIONS AND METHODS

RELATED APPLICATIONS

This application is a Continuation-In-Part application of U.S. patent application Ser No. 09/183,186 filed Oct. 30, 1998, Abandoned.

BACKGROUND OF THE INVENTION

1. Field of the Invention

The invention relates to chemical compositions and methods for using the compositions for simultaneously cleaning and decontaminating devices.

2. Description of Related Art

A variety of industries require that devices used within the industry be cleaned and decontaminated. Examples of two such sectors are the brewing industry and the medical arena. Such sectors require efficient and effective device cleaning and decontaminating foremost for health and safety reasons, but also for economic reasons.

Within the medical field, a variety of devices exist to serve important medical functions. Medical devices may be single-use or may be reusable. Cleaning and decontaminating products for medical devices may also be single-use or reusable and their associated methods or processes of application may be applied once or repeated. As used herein, decontamination is the removal of hazardous or unwanted materials such as bacteria, mold spores or other pathogenic life forms and the like, wherein high- and intermediate-level disinfection and sterilization represent different levels of decontamination. The time interval for achieving decontamination herein for medical devices other than kidney dialyzers is 30 minutes or less. No limitation is placed on the decontamination time useful for kidney dialyzers. These time intervals pertain to the time required to decontaminate a single medical device and do not apply to solution reuse time periods. Sterilization is a level of decontamination representing the complete elimination or destruction of all forms of microbial life, including fungal and bacterial spores. High-level disinfection is a level of decontamination representing a process that eliminates many or all pathogenic microorganisms, with the exception of bacterial spores, from inanimate objects.

Regulatory agencies and other groups have classified medical devices, processes, and cleaning and decontaminating products according to basic principles related to infection control. Medical devices are classified as critical, semicritical or noncritical. Critical devices, for example, scalpels, needles and other surgical instruments, enter sterile tissues or the vascular system. Such devices require sterilization with a process or with prolonged contact with a sporicidal chemical prior to reuse.

Semicritical devices, for example, flexible endoscopes, bronchoscopes, laryngoscopes, endotracheal tubes and other similar instruments, touch all mucous membranes except dental mucous membranes. Such devices require high-level disinfection with a process or short contact with a sporicidal chemical prior to reuse. High-level disinfection can be expected to destroy all microorganisms with the exception of high numbers of bacterial spores. An FDA regulatory requirement for high- and intermediate-level disinfectants is 100% kill of 1,000,000 organisms of *Mycobacterium tuberculosis* (*M. tuberculosis*) in the presence of 2% horse serum in a quantitative tuberculocidal test. This is a suspension test following the EPA Guidelines for the Quantitative Tuberculocidal Procedure. An additional FDA regulatory requirement for high-level disinfectants is that they must also achieve sterilization over a longer exposure time than the disinfection regimen time, as long as sterilization is achieved with 20 hours. The ability to achieve sterilization is measured by sporicidal activity as determined by the AOAC Sporicidal Test, AOAC Official Methods of Analysis, 15$^{th}$ edition, 1995. This test measures the ability of a solution to sterilize surfaces contaminated with dried bacterial spores. Spores of *Bacillus subtilis* ATCC #19659 and/or *Clostridium sporogenes* ATCC #3584 are used for this test. Common commercially available high-level disinfectants include glutaraldehyde solutions between 2.4–3.4%$^{w/v}$ which also typically require activation with an alkaline buffer just prior to use. Also available are an acidic (pH 1.60–2.00) hydrogen peroxide ($H_2O_2$) formulation comprising 7.5%$^{w/v}$ hydrogen peroxide and another antimicrobial agent (for example, Sporox®, Reckitt and Colman, Inc.), and an acidic mixture of 1.0%$^{w/v}$ $H_2O_2$ and 0.08%$^{w/v}$ peracetic acid (PAA) (Peract™ 20, Minntech Corp. or Cidex PA®, Johnson & Johnson). The minimum effective PAA concentration for high-level disinfection at 25 minutes (min) and 20° C. is 0.05%$^{w/v}$ (500 ppm) in the presence of 1.0%$^{w/v}$ $H_2O_2$ (Peract™ 20).

Medical devices such as thermometers and hydrotherapy tanks are also classified as semicritical, but they require intermediate-level rather than high-level disinfection prior to reuse. Intermediate-level disinfection inactivates *M. tuberculosis*, vegetative bacteria, most viruses and most fungi, but does not necessarily kill bacterial spores. A common intermediate-level disinfectant is Cavicide® (Metrex Research Corp.), which contains 0.28%$^{w/v}$ diisobutylphenoxyethoxyethyl dimethyl benzyl ammonium chloride, (a so-called super quat) and 17.2%$^{w/v}$ isopropyl alcohol.

Noncritical medical devices, for example, stethoscopes, tabletops, bedpans, etc., touch intact skin and require low-level disinfection prior to reuse. Low-level disinfection can kill most bacteria, some viruses, and some fungi, but it cannot be relied upon to kill resistant microorganisms such as tubercle bacilli or bacterial spores. Contact lenses are included in the class of devices which require low-level disinfection prior to reuse. Common low-level disinfectants for contact lens disinfection include acidic 3.0%$^{w/v}$ $H_2O_2$ and 1–10 ppm solutions of polymeric antimicrobial biguanides or quaternary ammonium compounds (e.g., 1 ppm polyhexamethylene biguanide in Complete® (Allergan Pharmaceuticals, Inc.) or 10 ppm Polyquad™ polyquaternary ammonium compound in Optifree® (Alcon, Inc.).

Standards for sterilization and low, intermediate and high-level disinfection have been concurrently established. These standards are based upon the known or possible risk of contamination of a particular medical device by a particular microorganism, the pathogenic nature of the organism and other principles in infection control. They typically require demonstration of sterilization and/or disinfection efficacy against a particular panel of test organisms, which collectively represent the known or possible contamination and infection risks. The test panels and criteria are different for low, intermediate or high-level disinfection. It is also generally accepted that a high-level disinfectant will meet the disinfection efficacy standards of intermediate- and low-level disinfection as well. It is universally accepted that low-level disinfection performance cannot predict intermediate- or high-level disinfection performance. In fact, it is assumed prior to testing that a low-level disinfectant cannot achieve a higher level disinfection standard. Additionally, other factors such as device compatibility with the disinfection system must also be considered. For example, no high-level disinfecting agent can be used for contact lens low-level disinfection because of the inherent incompatibility of the chemistry of the high-level disinfectants with either the contact lens, contact lens case or eyes with respect to neutralization requirements prior to wearing the lenses. Complicating this issue further is the introduction of cleaning agents into the overall disinfection care system.

Cleaning is the removal of all foreign material, including organic soil such as blood, feces, respiratory secretions, etc., from objects. It has been reported that failure to remove foreign material from a medical device such as an endoscope before a disinfection or sterilization process is likely to render the process ineffective. (Rutala, W A, APIC Guideline for Selection and Use of Disinfectants, *Am J Infect Control,* August 1996; Vol. 24,4:313–342). The presence of organic material or soil may contribute to the failure of disinfection by harboring embedded microbes and preventing the penetration of the germicide. Additionally, some disinfectants are inactivated by organic material (Martin, M A, Reichelderfer, M, APIC Guideline for Infection Prevention and Control in Flexible Endoscopy, *Am J Infect Control,* 1994;22:19–38). Major reasons reported for transmission of nosocomial infections related to endoscopes were inadequate cleaning, improper selection of a high-level disinfectant, or failure to follow recommended cleaning and high-level disinfecting procedures (Spach, D H, et. al., Transmission of Infection by Gastrointestinal Endoscopy and Bronchoscopy, *Ann Intern Med* 1993;118:117–28.). Current medical industry recommendations for the reprocessing of semicritical medical devices such as endoscopes call for meticulous physical cleaning to precede high-level disinfection and sterilization procedures (Simmons, B P, Guideline for Hospital Environmental Control, *Am J Infect Control* 1983;11:97–115; Rutala, W A et. al., Disinfection Practices for Endoscopes and Other Semicritical Items, *Infect Control Hosp Epidemiol,* 1991;12:282–8). An additional problem is that coagulated blood can build up and lead to blocking of the various channels of a flexible fiberoptic endoscope. It is difficult to effectively remove organic material such as blood, mucus and feces from the narrow channels and exterior sections of flexible fiberoptic endoscopes. Ineffective removal of deposits results in costly routine maintenance to prevent blockages.

Current recommendations for cleaning and high-level disinfecting of semicritical medical devices such as flexible endoscopes and other similar instruments have been published. In general, endoscope disinfection involves six steps: (1) clean—mechanically clean external surfaces, ports and internal channels with water and a detergent or enzymatic detergent; (2) rinse—rinse and drain channels with water; (3) disinfect—immerse endoscope in high-level disinfectant, perfuse disinfectant into suction and biopsy channel and air and water channel and expose for at least 20 min; (4) rinse—the endoscope and channels should be rinsed with sterile water; if this is not feasible use tap water followed with an alcohol rinse; (5) dry—the insertion tube and inner channels should be dried by forced air after disinfection and before storage; and (6) store—the endoscope should be stored in a way that prevents recontamination (Martin, M A, Reichelderfer, M, APIC Guideline for Infection Prevention and Control in Flexible Endoscopy, *Am J Infect Control,* 1994;22:19–38). Cleaning of endoscopes should be performed promptly after use to prevent drying of soils. Additionally, before cleaning, all endoscope channels should be irrigated with copious amounts of detergent and tap water to soften, moisten, and dilute organic debris.

Liquid enzymatic detergents used with semicritical medical devices are known also as enzymatic presoak and cleaning solutions. They are designed to be diluted with water at between ½ and 1 ounce per gallon of water prior to use and it is recommended they be used to presoak medical devices for between a few and 10 min or more. Users typically have the option to prepare the solution daily or more frequently if the solution is visibly soiled. Thus, current enzymatic detergents are reused over the course of one day. Soil antiredeposition agents are added to some formulas to facilitate solution reuse by preventing the redeposition of previously solubilized soils onto the next device placed into the cleaning solution.

High-level disinfecting solutions are also typically designed for a reuse option, depending upon the medical device. For example, a glutaraldehyde high-level disinfecting solution for endoscope reprocessing may be reused for as long as 28–30 days, while kidney dialyzers are disinfected with single-use solutions. The principle reason for reusing a solution is economic, as the practice itself provides the opportunity for adding to the risk of transmission of infection.

Thus, current medical device industry practices for semicritical medical devices such as endoscopes involve separate short cleaning and disinfecting steps and times, and reusable solutions. Longer soak cleaning or disinfecting times and single-use solutions would for the most part be impractical and uneconomical in the current environment.

Kidney dialyzers pose an additional problem in high level disinfecting in that the materials utilized require particular performance criteria of the cleaning and disinfection solutions. Types of dialyzers include: (1) coil, which incorporates a membrane in the form of a flattened tube wound around a central, rigid cylinder core, with a supporting mesh between adjacent portions of the membranes; (2) parallel plate, which incorporates a membrane in tubular or sheet form supported by plates in a sandwiched configuration; and (3) hollow-fiber, which incorporates the semipermeable membrane in the form of the walls of very small fibers having a microscopic channel running through them. Most parallel plate and hollow-fiber membranes are made from cellulose acetate, cellulose triacetate, regenerated cellulose, cuprophan or polysulfone. The semipermeable membranes used in dialyzers have large areas and high porosities, and after use become coated with blood proteins and other organic and cellular material. Dialysis fibers are also often clotted with blood cells, proteins and other debris. As a result, the membrane of a used dialyzer has a reduced capacity for dialysis and is highly susceptible to microbial growth. Effective killing of microorganisms on such a used membrane for the purpose of reusing the dialyzer is difficult to accomplish without damaging the membrane. When initially introduced, dialyzers were one-use devices. Since 1980, dialyzer reuse has risen dramatically in order to reduce the overall cost to the patient and the health care delivery system. Hemodialyzers, reprocessed in conformance with the Association for the Advancement of Medical Instrumentation (AAMI) specific guidelines and performance tests, have an average use number, that is, the number of times a particular hemodialyzer has been used in patient treatment. This number has been increasing over the years, from a United States average of 10 reuses in 1986 to 15 reuses in 1996. The cost benefits achieved by reprocessing are significant. For example, a new dialyzer costs about $20–30. With reprocessing, a dialyzer can be used between 5–20 times without substantial loss of efficacy. The cost of reprocessing is approximately $6.60–7.72 per unit, including reprocessing solutions. The cost per reuse for reprocessing solutions is $0.99–1.14 (average $1.08). The amortized dialyzer cost per reuse is $1.35–2.00, based upon an average reuse of 15 times. Additionally, the cost per reuse for dialyzer hazardous medical waste disposal is $0.50–0.55, reuse technician labor costs are $14/hr, and the associated labor cost of manual cleaning/dislodging clots is $0.23. Accordingly, with reprocessing, the dialyzer cost per treatment is conservatively less than about $10, as opposed to $30 if a new dialyzer were used for each treatment. A typical patient receives approximately 156 treatments per year. In 1998 in the United States alone there were approximately 280,000 patients on hemodialysis, and about 86% of hemodialysis centers have a dialyzer reuse program. Therefore, there are about 35,060,480 reuses in the United States (280,000×0.86×(156–156/15)). The U.S. market for reprocessing solutions in 1998 is estimated to be $34.7–40.0 million. The number of patients on dialysis in the United States is growing at the rate of 7% per year. Additionally, the dialyzer reuse incidence of 86% in 1998 is expected to grow 2% per year to essentially 100% reuse by the year 2005. Utilizing a 3% rate of product price inflation, the United States market for reprocessing solutions is expected to be $83 million by the year 2005. Worldwide, the market for current generation reprocessing solutions is expected to be 1.5 times the United States market, or $125 million by the year 2005. The worldwide market has the potential to be much larger, as the prevalence rates of people on dialysis are expected to be greater than 1000 persons per million population in the United States, Japan and some European countries by the year 2000. Conceivably, 5 million people or more could be on dialysis worldwide if United States medical practices were fully adopted. This translates to a potential reprocessing solution market of $793 million in current dollars, based upon 145 solution uses per year per patient at $1.09 current cost per solution use.

In addition to cost savings with dialyzer reuse, there are health advantages. Researchers have determined that reused dialyzers significantly mitigate patients' "new dialyzer" symptoms as well as immune reactions that often occur. The inherent clinical advantage of reused dialyzers has been attributed to both the reduction in trace contaminants such as ethylene oxide sterilant, and to the masking of immune reaction sites located on the membrane surface by protein deposits.

Dialyzer reprocessing involves three basic steps: (1) cleaning, (2) dialysis efficacy confirmation, and (3) high-level disinfecting involving soak times long enough to achieve sterilization. The cleaning step involves removing residual blood, organic and cellular material from the blood side and removing dialysate from the dialysate side of the semipermeable membrane. A number of cleaning solutions are known, including sodium hypochlorite bleach, PAA and $H_2O_2$. Purified water has also been used for cleaning. The cleaning solution must be rinsed from the dialyzer, typically with water.

Sodium hypochlorite bleach at a concentration of 0.5–1.0%$^{w/v}$ for 3 min exposure is utilized for cleaning. However, significant decreases in patient urea and creatinine clearance have been observed with high-flux polysulfone (F80B) dialyzers reprocessed with formaldehyde and bleach (Murthy et. al., Effect of Formaldehyde/Bleach Reprocessing on In Vivo Performances of High-Efficiency Cellulose and High-Flux Polysulfone Dialyzers. *J Am Soc Nephrol*:464–472, 1997). Also, Kaplan and colleagues observed up to 20 g blood protein and specifically 15 g albumin loss into the dialysate per treatment with bleach-reprocessed, high-flux polysulfone (F80) dialyzers. Elimination of bleach from the reprocessing protocol led to a significant increase in serum albumin levels. (Kaplan et. al., Dialysate Protein Losses With Bleach Processed Polysulfone Dialyzers. *Kidney Int* 47;573–578, 1995.) It is believed that reprocessing certain polysulfone dialyzers with bleach somehow alters membrane structure. Loss of the usual immune protection achieved with reused dialyzers has been shown to occur when sodium hypochlorite, particularly at elevated concentrations, is used for reprocessing, resulting in complement activation and neutropenia restored to near original levels. The problems associated with utilizing bleach in the reprocessing protocol have widespread ramifications; in the U.S. as of 1996, 42% of all patients were utilizing high-flux dialysis and 78% of those were utilizing polysulfone dialyzer membranes. Finally, while not reported within the kidney dialysis industry, it is known that chlorine bleach solution has a tendency to form so-called haloforms with organic compounds. These compounds are considered to be carcinogenic and are therefore also hazardous from the health perspective. In this context, it was recently reported that dialysis patients had an increase in cancer of 15% as compared to the general population (*The Lancet*, 354, 93–99, 1999).

Dialyzers reprocessed with $H_2O_2$-containing solutions have a significant reduction in ultrafiltration rate, indicating the presence of hydrolytically resistive protein deposits resistive to removal by $H_2O_2$. In addition, while $H_2O_2$-containing solutions are useful in that they react vigorously with hemoglobin, can be effective in dissolving some clots in dialyzer headers and blood channels, and can restore dialyzer fiber bundle volume in some cases, elevated concentrations of $H_2O_2$ can rapidly generate gaseous oxygen reaction products, as evidenced by the reported bursting of noncompliant membrane capillary fibers. PAA reacts similarly with protein deposits, as PAA contains an equilibrium mixture of $H_2O_2$, PAA and acetic acid. Thus, PAA will not remove protein deposits but can be effective in dissolving some clots.

Lastly, water used in the reprocessing cleaning step is generally ineffective in removing protein deposits or bound clots, as is the case with formaldehyde and glutaraldehyde.

The use of citric acid in connection with the cleaning of dialysis machines has been disclosed in a number of patents. Tell et al., U.S. Pat. No. 4,690,772, discloses a sterilizing and cleaning solution comprising sodium chlorite, citric acid and a sodium bicarbonate buffer. U.S. Pat. No. 5,480,565 to Levin discloses a method for reprocessing dialyzer cartridges used with kidney dialysis machines. The method involves filling the blood and dialysate compartments of the dialyzer with an aqueous solution containing citric acid at a concentration of about 1.0–5.0%$^{w/v}$ and then subjecting the dialyzer to an elevated temperature above 90° C. and below 100° C. for a period of at least 15 hours (h). It is known, however, that citric acid is incapable of removing bound protein deposits from polymer surfaces at these temperatures. Moreover, the sodium chlorite solutions in the '772 patent have the capacity to crosslink proteins in surface deposits, making them even more resistant to removal. Also, the heat utilized in the '565 patent will further denature proteins and possibly create more deposits, as well as deposits which are more resistant to removal.

The efficacy confirmation step for dialyzer reprocessing involves confirming that membrane integrity and performance is substantially equivalent to that of a new dialyzer.

Specifically, with respect to membrane performance, when the measured fiber bundle volume (FBV) of the membrane drops by 20%, the dialyzer is no longer reused.

The disinfection step involves subjecting the dialyzer to high level disinfection with a process or chemical disinfecting agent. Chemical disinfecting agents such as formaldehyde, glutaraldehyde or an equilibrium mixture of PAA, $H_2O_2$ and acetic acid are typically employed. In the United States in 1996, 36% of dialysis centers used formaldehyde, 54% used PAA, 7% used glutaraldehyde and 3% used heat to disinfect and sterilize. A commonly used glutaraldehyde solution is Diacide® (Gulfstream Corp.) a 26%$^{w/v}$ concentrate of acidic glutaraldehyde which is activated with alkali just prior to use and then diluted with water to a final concentration of 0.8%$^{w/v}$. In 1998, the most commonly used PAA-based product was Renalin® Dialyzer Reprocessing Concentrate (Renal Systems Division, Minntech Corp). Renalin® is a concentrated solution of 4%$^{w/v}$ PAA and 24%$^{w/v}$ $H_2O_2$, designed to be diluted to a 3.5%$^{w/v}$ concentration in water, yielding a final concentration of 0.14%$^{w/v}$ (1400 ppm) PAA and about 0.84%$^{w/v}$ (8400 ppm) $H_2O_2$.

The chemical disinfecting agent must be able to be rinsed out of the dialyzer to below toxic levels, with a rinse-out period established for the particular agent. Typically, for glutaraldehyde disinfectants, 1 liter of isotonic sterile saline is perfused through the dialyzer fibers prior to dialyzer use, with sterile purified water additionally used to rinse the dialysate chamber. Moreover, since the dialyzer is connected to the vascular system during use, any residual chemical entity which may be reversibly bound to the semipermeable membrane and which may desorb from the dialyzer following the rinse should be non-immunogenic, i.e., it should not provoke an immune response.

PAA compositions for cleaning, or cleaning and low level disinfecting, have been disclosed in several publications. UK patent application GB 2129458 A filed Oct. 24, 1983 by Tatin and assigned to PCUK Produits Chimiques Ugine Kuhlmann discloses single-use washing compositions comprising an alkali metal perborate and an activator for decomposing the perborate to PAA, the activator selected from cyanamide and metal salts thereof, and a proteolytic enzyme obtained from a strain of bacillus. The perborate is preferably sodium perborate, used at a standard concentration for a washing powder of 15%$^{w/v}$ or 1 g/l of bath and produces a $H_2O_2$ concentration of 0.0220%$^{w/v}$ (220 ppm). The quantity of cyanamide activator is between 2–8%$^{w/w}$ of the total washing agent, corresponding to 0.0133–0.0533%$^{w/v}$ (133–533 ppm). The concentration of PAA produced by the aforementioned mixture of 220 ppm $H_2O_2$ and 533 ppm activator is not represented, but cannot exceed 220 ppm. These concentrations of PAA and remaining $H_2O_2$ (if any) are well below the minimum effective concentration of 500 ppm PAA and 1.0%$^{w/v}$ $H_2O_2$ to achieve high level disinfection in 25 min and sterilization in a longer time interval.

Gray, U.S. Pat. No. 3,714,050 discloses a dry single-use composition containing sodium perborate, a proteolytic enzyme and $MgSO_4$ for removing stains from fabrics. In the preferred form the composition contains a perborate activator which produces a percarboxylic acid. A preferred perborate range is one which provides a concentration of "per" compound (e.g., a compound with or containing the chemical structure R—O—O—R$^1$, wherein both R and R$^1$ can be H or another chemical group such as an acetyl group or a metal ion or another inorganic or organic atom or chemical group) in the soaking water equivalent to about 5–200 ppm of available oxygen. These compositions thus provide a PAA and remaining $H_2O_2$ concentration (if any), which are well below the minimum effective concentration of 500 ppm PAA and 1.0%$^{w/v}$ $H_2O_2$ required to achieve high level disinfection in 25 min and sterilization in a longer time interval.

Sarot, U.S. Pat. No. 3,816,319 discloses a process for activating peroxide compounds in aqueous solutions used for washing and bleaching or for unspecified decontamination and disinfection and also solid single-use compositions containing both a peroxide compound and the activator. The process includes activating peroxide compounds selected from the group consisting of $H_2O_2$, sodium perborate and sodium percarbonate, with the activator selected from the group consisting of diacylated glyoxime and diacylated dialkylglyoxime. The solid compositions comprise either sodium perborate or sodium percarbonate and an activator selected from the group consisting of diacylated glyoxime or diacylated dialkylglyoxime. Laundry cleaning tests were carried out with washing powders containing either 2 g/l of sodium perborate or sodium percarbonate, proteolytic enzymes and diacetylated dimethylglyoxime at a concentration of 0.35–0.40 g/l. These compositions will produce $H_2O_2$ at a concentration of 440 ppm from the sodium perborate and a somewhat higher concentration of $H_2O_2$ from the sodium percarbonate. The concentration of PAA produced by the aforementioned mixture of $H_2O_2$ and 400 ppm glyoxime activator is not represented, but can be estimated to be on the order of 400 ppm or less. The concentrations of PAA and $H_2O_2$ (if any remains) are well below the minimum effective concentration of 500 ppm PAA in the presence of 1.0%$^{w/v}$ $H_2O_2$ required to achieve high level disinfection in 25 minutes and sterilization in a longer time interval.

Patents for compositions and methods for cleaning and disinfecting a variety of medical devices have also issued. Some of the following disclosed compositions and methods are commercially available.

Knepper, German Patent No. 2,130,833 issued Jan. 11, 1973, discloses cleaning and disinfecting compositions for medical devices, especially tubular suction devices, comprising a mixture of protein-degrading enzymes, quaternary ammonium base for disinfection and other known cleaning agents such as phosphates and nonionic builders. However, quaternary ammonium base disinfecting compounds are suitable only for low level disinfection when used alone, that is, without other disinfecting agents. Neither the level of disinfection nor the enzymes are specified, however, an extremely long exposure of 12–48 hours is claimed to achieve cleaning: Additional surfactants, metal corrosion inhibitors, chelating agents, buffers and soil redeposition inhibitors are not disclosed. The '833 patent does not pertain to reusable cleaning and disinfecting solutions.

Huth, U.S. Pat. No. Re. 32,672 discloses a one step method for simultaneously cleaning and disinfecting contact lenses comprising contacting the lenses with a solution comprised of a disinfecting amount of peroxide and an effective amount of peroxide-active proteolytic enzyme for a time sufficient to remove substantially all protein accretions and to disinfect the lenses. The preferred peroxide is $H_2O_2$ in a preferred amount of 3%$^{w/v}$, however, an amount of 10%$^{w/v}$ or more is also disclosed, limited only by the requirement that the enzyme retains proteolytic activity. A disinfecting amount of peroxide is defined as the amount that will reduce the microbial burden by one logarithm in three hours. The microbial burden and disinfection pertain solely to microorganisms contaminating contact lenses and the low-level disinfecting standards required by the Food and Drug Administration (FDA) for antimicrobial testing of contact lens disinfecting products. These low-level disinfection standards are based upon antimicrobial efficacy testing against particular panels of test organisms, the USP XXI Panel and the FDA "Soft Lens" Panel, both of which are representative of the types of organisms found specifically on contact lenses. Thus, disinfection in the '672 patent does not pertain to the standards for intermediate- and high-level disinfection of other medical devices such as endoscopes and kidney dialysis devices, the latter of which requires high-level disinfection, nor does the it pertain to sterilization of medical devices. The '672 patent discloses that the enzymes may be derived from any plant, animal or microbial source and may be acidic, neutral or alkaline. Additional surfactants or soil redeposition inhibitors are not disclosed. Corrosion inhibitors to prevent metal part or adhesive corrosion are not disclosed, as contact lenses do not contain metal parts or adhesives. Chelating agents are also not disclosed. The '672 patent also does not pertain to reusable cleaning and disinfecting solutions.

Disch, U.S. Pat. No. 5,234,832 discloses a process for cleaning and disinfecting surfaces of heat and corrosion sensitive medical instruments with an aqueous cleaning and disinfecting solution. The process comprises, in successive steps, (a) contacting the surfaces to be cleaned and disinfected for about 1–15 min with the aqueous detergent and disinfectant solution at pH between 6–8 and a temperature of about 55° C.–65° C. and which contains (1) water having a hardness of 3–8 German hardness (Gh) units, (2) at least one low foaming nonionic surfactant (3) at least one proteolytic enzyme (4) at least one complexing agent (5) at least one aldehyde disinfectant selected from the group consisting of formaldehyde and aliphatic dialdehydes containing 2–8 carbon atoms; (b) rinsing the surfaces at least twice with water having a hardness of 3–8 Gh and at a temperature of about 55° C.–65° C. at least in the last rinse cycle; and (c) drying the surfaces with sterilized air at a temperature of about 40° C.–60° C. The addition of soil redeposition inhibitors is not disclosed, nor are specific metal corrosion inhibitors. Aliphatic dialdehydes utilized in the '832 patent include glutaraldehyde, which is a commonly used high-level disinfectant for medical devices such as endoscopes. The '832 patent utilizes proteolytic enzymes obtained from bacterial strains of the same type utilized in the '672 patent. It is known, however, that bacterial proteolytic enzymes such as subtilisin retain little activity in the presence of glutaraldehyde at a concentration suitable for high-level disinfection, thus no functional cleaning would occur. The '832 patent also does not pertain to reusable cleaning and disinfecting solutions.

Huth, U.S. Pat. No. 5,356,555 discloses a method for simultaneously cleaning and disinfecting a contact lens, comprising the steps of (1) forming a disinfecting solution comprising polyhexamethylene biguanide and other excipients, (2) providing an effective and efficacious amount of subtilisin A proteolytic enzyme, (3) combining the contact lens, the disinfection solution and the subtilisin A and (4) soaking the lens in the resulting solution for a period of time sufficient to clean and disinfect. Enzymes disclosed in the '672 patent are also employed in the '555 patent. Again, the microbial burden and disinfection pertain solely to microorganisms contaminating contact lenses and the low-level disinfection standards required by the FDA for antimicrobial testing of contact lens disinfection products. Surfactants are disclosed. The use of soil redeposition inhibitors is not taught; however, two of the most commonly used soil redeposition inhibitors, carboxymethylcellulose and hydroxypropylmethylcellulose, are disclosed. The '555 patent teaches that carboxymethylcellulose and hydroxypropylmethylcellulose can be used in amounts to detoxify the active disinfecting agent. Again, corrosion inhibitors to prevent metal part or adhesive corrosion are not disclosed as contact lenses do not contain metal parts or adhesives. The '555 patent also does not pertain to reusable cleaning and disinfecting solutions.

Beerstecher, U.S. Pat. No. 5,571,488 discloses an apparatus which utilizes an improved method to enable an optimum hygienic preparation of medical and dental instruments. Instruments are placed into a chamber that can be closed pressure-tight and in which the following steps can be automatically sequenced in a preselected process. The steps of the method comprise (a) cleaning the exterior surfaces of the instrument as well as potentially any media channels with a high-energy water jet directed onto the instruments, first with cold water and subsequently with pre-heated water, (b) intensive after-cleaning and disinfection of the exterior surfaces and, potentially, of the media channels as well as of the moving internal parts and their bearings by blowing off and out with a water stream at a temperature between approximately 60° C.–100° C. (c) caring for the moving internal parts and their bearings of the instrument by injecting a metered quantity of lubricant (d) sterilizing the instruments inside and out with saturated water steam at a temperature of, preferably, 130° C. and then (e) drying and cooling the instruments with a coolant, preferably compressed air. The '488 patent does not pertain to a chemical-based system employing cleaning and disinfecting agents, nor does it pertain to reusable cleaning and disinfecting solutions.

None of the above cleaning and disinfecting systems provides for a simple and easy to use, functional, single use or reusable system for simultaneous cleaning and decontaminating devices such as medical devices (e.g., endoscopes). None of the above systems provide for a simple, functional single use or reusable system for simultaneous cleaning and high-level disinfecting or sterilizing a kidney dialyzer. Thus, there is a need for improved compositions and methods for such applications.

SUMMARY OF THE INVENTION

The invention is directed to a composition to simultaneously clean and decontaminate (i.e., sterilize or high-level disinfect) a device, for example a medical devise such as an endoscope or a kidney dialyzer. The composition is a per-compound oxidant, such as hydrogen peroxide ($H_2O_2$) and/or peracetic acid (PAA) and an enzyme. The enzyme may be proteolytic, human or non-human, and may be active at an acid, alkaline or neutral pH. Examples of enzymes are include subtilisin, trypsin, chymotrypsin and pepsin. Preferred concentrations are 0.5–50%$^{w/w}$ $H_2O_2$, 0.05–5%$^{w/w}$ PAA and 0.00001–10 Anson Units (A.U.)/ml enzyme. The composition may also include a corrosion inhibitor to prevent corrosion of a metal device, a chelator, a buffer, a dye or combinations of these. The composition may be reused to simultaneously clean and decontaminate a plurality of devices and the composition may be periodically recharged with enzyme.

The invention is also directed to a method to simultaneously clean and decontaminate a device after removing loosely adhering soil from the device, for example, by manually removing soil with a cloth and/or by rinsing with water or with an enzyme or non-enzyme detergent. The device is then contacted, for example by immersing the device in the composition, with the composition of the invention as described above. The composition can then be removed from the device, for example, by rinsing with sterile water or saline. These steps can be performed on a plurality of devices while reusing the same composition. The device can rinsed with alcohol, dried and stored to prevent recontamination.

A preferred composition includes about 0.05–5%$^{w/w}$ PAA, about 0.001–2.0 A.U./ml protease with the protease in solution concentrate form to be diluted in the PAA solution, and about 0.05–5.3%$^{w/v}$ chelator, with the composition having a pH between 5–9. Another particularly preferred composition includes about 0.10–1.0%$^{w/v}$ of a corrosion inhibitor in the previous composition and the composition having a pH between 1–5. Particularly preferred methods include contacting one or more medical devices with these compositions.

A particularly preferred composition to simultaneously clean and decontaminate a kidney dialyzer is a mixture of about 0.5–1.5%$^{w/w}$ $H_2O_2$, about 0.05–3.0% $^{w/w}$ PAA, and about 0.00001–0.10 A.U./ml human pepsin, with the composition having a pH between 1–6. Another particularly preferred composition to simultaneously clean and decontaminate a kidney dialyzer is a mixture of about 0.5–1.5%$^{w/w}$ $H_2O_2$, about 0.05–3.0%$^{w/w}$ PAA and about 0.00001–0.10 A.U./ml human trypsin, with the composition having a pH between 6–9. In a particularly preferred method, the ends of the fiber bundles of the dialyzer are contacted with either of the previously described compositions.

It will be appreciated that the disclosed simultaneous cleaning and decontaminating compositions and methods of the invention have a wide array of applications. These and other advantages of the invention will be further understood with reference to the following drawing, detailed description and examples.

BRIEF DESCRIPTION OF THE DRAWING

The FIGURE is a graph of the results of simultaneously cleaning and decontaminating a kidney dialyzer.

DETAILED DESCRIPTION OF THE INVENTION

It has been discovered herein that despite the complete inactivation of certain bacterial proteases with high concentrations of per-compound oxidants such as peracetic acid ($CH_3COOOH$, hereafter abbreviated as PAA) and mixtures of hydrogen peroxide and PAA required to achieve decontamination, represented herein as high- or intermediate-level disinfection and/or sterilization, one can nonetheless combine selected cleaning enzymes with per-compound solutions to achieve single-use simultaneous cleaning and decontamination (high- or intermediate-level disinfection or sterilization) of a device such as an endoscope. Moreover, it has been discovered herein that through the proper selection of an amount of chelating agent and pH buffer of appropriate hydrophobicity, along with the application of medical device reprocessing steps involving a first bulk soil removal step followed by contacting the device with a combined solution of enzyme and per-compound, then rinsing the solution from the device and thereafter repeating the reprocessing steps for each device, one can achieve a simultaneous cleaning and decontaminating solution and method which is reusable for processing a plurality of medical devices such as endoscopes. Moreover, longer solution reuse times can be achieved with a method step wherein the enzyme is added to the solution in intervals so that enzyme activity is replenished. Additionally, it has been discovered that metal corrosion inhibitors can be combined with cleaning enzymes and per-compounds without inactivating the cleaning activity of the enzymes. The compositions of the present invention can also be prepared as a concentrate designed to be diluted with water to a final use dilution just prior to use. The compositions and methods of the present invention can be used through either manual or automated instrument applications, at various temperatures and with ultrasonic or other energy input.

It has also been discovered herein that the compositions and methods of the present invention can be utilized for safely and efficiently simultaneously cleaning and decontaminating an artificial kidney dialyzer, such that dialyzer reuse life can be significantly extended.

Advantages of the Present Invention

One advantage of the compositions and methods of the present invention is the reduced number of device processing steps. Prior art methods employ an initial separate precleaning treatment with an enzymatic detergent, followed by a rinsing step, followed by a disinfecting step, and thereafter a last rinsing step. The method of the present invention includes an optional first bulk soil removal rinsing step, followed by a simultaneous cleaning and decontaminating step employing a per-compound oxidant and an enzyme, and a last rinsing step to remove the oxidant and enzyme solution from the device. Thus, the invention combines the former separate enzymatic detergent precleaning treatment with the decontaminating step so that cleaning and decontaminating are performed simultaneously. There are several advantages of this combination, such as (1) the reduced number of device processing steps making processing easier, faster and hence less costly for the user; (2) the enhancement of enzymatic cleaning, which takes place with the combination of enzyme and decontaminant, that results in better cleaning and hence longer device lifetime; and (3) regimen compliance is imposed, with the result that proper cleaning is carried out so proper decontamination is ensured. The latter advantage is perhaps the most significant, as non-compliance with proper device cleaning can result in insufficient decontamination/sterilization and infection.

A second advantage is that the combined cleaning and decontaminating solution is reusable. This is due to the incorporation of a combination of enzyme plus decontaminant plus a unique chelating agent and/or buffer, the latter which provides adequate buffering capacity for a large volume of decontaminant during multiple device processing cycles. The chelating agent in the proper concentration prevents destabilization of the decontaminant due to contact with blood and trace metals. The reusability of the compositions of the present invention is also made possible by the unique device reprocessing steps employing a bulk soil removal rinsing step, followed by a simultaneous cleaning and decontaminating step employing a per-compound oxidant and an enzyme, and a last rinsing step to remove the oxidant and enzyme solution from the device. The foregoing steps are then repeated for a plurality of devices such as a medical device wherein each device is contacted with the same per-compound oxidant and enzyme composition. Either of the aforementioned removal steps can be accomplished with distilled, pyrogen-free, microbe-free (e.g., sterile) or tap water, the latter which is particularly convenient for the user when employed in the first bulk soil removal step. Alternatively, the first bulk soil removal rinsing step can be optionally performed with either an enzyme-containing or non-enzyme detergent. The latter type of detergent would be more preferred over an enzyme detergent. Additionally, the first removal step can be preceded by a manual soil removal step employing a sponge, cloth or towel. The final solution removal step can be followed by storage of the device in a way which prevents recontamination either by microorganisms or soils. The final solution removal step can also be followed by a drying step with air or other means. This step in turn can be followed by storage of the device in a way which prevents recontamination either by microorganisms or soils. The final solution removal step can also be followed by an alcohol rinse step, which in turn can be followed by a drying step with air or other means and thereafter by storage in a way that prevents recontamination. An even simpler medical device reprocessing regimen includes: a) contacting the medical device with a solution comprising a per-compound oxidant in an amount effective to achieve decontamination and an enzyme in an amount effective for cleaning the device, wherein the decontaminating and cleaning occur simultaneously; and b) removing the solution from step a) from the device. An even simpler medical device reprocessing regimen includes only step a) above. These simplified steps can be preceded or followed by additional reprocessing steps for soil removal, drying, alcohol rinsing and storage to prevent recontamination as above. All of the foregoing steps can be repeated to reprocess a plurality of devices such as medical devices. These foregoing methods provide simplified, convenient reprocessing regimens for devices. The compositions of the present invention, employing the methods of the present invention, can extend solution reusability for a plurality of devices, preferably between about one-five days, although solution reuse for much longer periods of up to thirty days is possible, the latter especially wherein a non-enzyme detergent is utilized for the first bulk soil removal rinsing step.

A third advantage is that the combination of enzyme plus decontaminant may include a corrosion inhibitor which is compatible with both the enzyme and the disinfectant. The corrosion inhibitor may be necessary when using the compositions and methods of the present invention for devices containing metal parts and adhesives.

Another advantage of the present invention is that the combination of enzyme plus disinfectant can also be prepared as a concentrate designed to be diluted with distilled, tap or other water to a final use dilution just prior to use. Additionally, either the enzyme-containing solution or the decontaminant solution can be prepared as a concentrate and then mixed with the other and with distilled, tap or other water as needed just prior to use. The use of concentrates reduces product shipping and storage requirements, making the system more convenient.

An additional advantage is the cost savings over existing chemical reprocessing solutions. For example, the compositions and methods of the present invention for kidney dialyzer reprocessing can extend dialyzer life two-five times or more. A two-fold improvement in dialyzer life extends the average reuse to 30 times, reducing the amortized dialyzer cost per reuse to $0.68–1.00 and yielding an equal amount saved. Also, there are savings on hazardous waste disposal of $0.25–$0.28 (($0.50/2)–($0.55/2)). Lastly, savings of $0.23 would be obtained due to elimination of the labor cost of manual cleaning/dislodging of clots. Thus, total cost savings per reuse ranges from $1.16 (15–18% of the total reuse cost range) to $1.51 (20–23%). Similarly, cost savings incurred with a four-fold improvement in dialyzer life ranges from $1.63 (21–25%) to $2.14 (28–32%) per reuse. Moreover, considering that these cost savings are achieved with the new reprocessing solutions of the present invention, a higher product price can be justified. An additional price of $1.07 or more can be justified (one-half or more of the cost savings). Combined with the 1998 cost average of $1.09 for prior art reprocessing solutions per use, a total product price of $2.16 or more can be justified. Thus, the world market for reprocessing solutions can be doubled from the current forecast of $125 million in the year 2005 to $250 million.

Still another advantage of the methods and compositions of the present invention is that efficient cleaning of a dialyzer can take place safely during decontamination, such that the biocompatibility of the dialyzer is maintained or even enhanced, rather than compromised as when cleaned with sodium hypochlorite bleach. The compositions and methods of the present invention efficiently remove cellular debris and protein deposits while leaving at least a partial monomolecular layer of protein remaining to mask immune reaction sites located on the dialyzer membrane surface. At the same time, this thin layer of remaining protein does not compromise dialyzer ultrafiltration performance due to its thinness.

Still another advantage of the methods and compositions of the present invention is that, unlike the present cleaning compositions and methods utilizing bleach, dialyzer fibers will not be damaged with solution exposure times exceeding a few minutes.

Still another advantage is that the preferred human enzymes for dialyzer cleaning will not provoke an immune response if they enter the circulatory system in amounts arising from desorption from the dialyzer fibers following the final rinsing step employed just prior to dialyzer use, and the preferred non-human enzymes will not provoke an immune response because they have little to no interaction or binding with the dialyzer fibers, resulting in an insufficient amount of material desorbing from the fibers into the blood during dialysis to provoke an immune response. Additionally, it may be advantageous to clean a dialyzer by contacting only the ends of the fiber bundle, which are readily isolated from the remaining portion, with the simultaneous cleaning and decontaminating solution. This may limit an immunogenic response in comparison to a response produced by contacting the entire portion of the fiber bundle with the solution.

An additional advantage is that the solution does not have the capability to transform organic compounds within the dialyzer into carcinogenic haloforms as does chlorine bleach.

The following provides a detailed description of the invention regarding specific elements of the compositions, methods of use and applications.

Composition

Enzymes

Source

A single enzyme or a mixture of several enzymes may be employed in the present invention. At least one enzyme used herein is preferably proteolytic in nature, that is, it has at least partial capability to hydrolyze peptide-amide bonds, which in turn reduces proteinaceous material deposited on a device or instrument to smaller water-soluble peptide or amino-acid subunits. Proteolytic enzymes may be endoproteases or exoproteases or a combination of both types. Other enzymes exhibiting amylolytic or related carbohydrase activities and/or lipolytic or lipase activities may also be employed. Enzymes may exhibit alkaline, neutral or acidic pH activity profiles and may additionally be thermally stable. Enzyme raw materials may exhibit some lipolytic, amylolytic or related activities associated with the proteolytic activity. Enzymes may be derived from any plant or animal source, including human, other mammalian sources and microbial sources, as long as they meet all of the requirements of the particular application within the scope of the present invention, i.e., human enzymes are preferred for kidney dialyzer reprocessing applications to minimize foreign enzyme immunoreactivity.

A thermally stable or thermophilic enzyme is stable and active at temperatures >50° C. or even >100° C. One such heat stable protease is thermolysin and others may be obtained at pages 642–650 of Perlmann et al., "Proteolytic Enzymes," Methods in Enzymology, Volume XIX, Academic Press (1970), which pages are specifically incorporated by reference herein.

Examples of suitable proteolytic enzymes include but are not limited to pancreatin, trypsin, chymotrypsin, collagenase, keratinase, carboxylase, aminopeptidase, elastase, aspergillo-peptidases A and B, pronase E (from *S. griseus*), dispase (from *Bacillus polymyxa*) and mixtures thereof. Metalloproteases, enzymes which contain a divalent metal ion such as calcium, magnesium or zinc bound to the protein, and acid proteases such as pepsin may also be utilized.

The preferred group of proteolytic enzymes for non-dialyzer applications are microbially derived such as those derived from Bacillus, Streptomyces and Aspergillus species. Microbially derived enzymes are disclosed in U.S. Pat. No. 4,690,773 which is expressly incorporated herein by reference in its entirety. Reference is also made to Keay, L, Moser, P W and Wildi, B S, "Proteases of the Genus Bacillus. II Alcaline Proteases," Biotechnology and Bioengineering, Vol. XII, pp. 213–249 (1970) and Keay, L and Moser, P W, "Differentiation of Alkaline Proteases from Bacillus Species", Biochemical and Biophysical Research Comm., Vol. 34, No. 5, pp. 600–604 (1969). Most preferred are the Bacillus derived alkaline proteases generically called subtilisin enzymes.

The subtilisin enzymes include subtilisin A and subtilisin B sub-classes. Subtilisin A includes enzymes derived from such species as *B. subtilis, B. licheniformis* and *B. pumilis* and produce little or no neutral protease or amylase. Subtilisin B includes enzymes from such organisms as *B. subtilis, B. subtilis* var. amylosacchariticus, *B. amyloliquefaciens* and *B. subtilis* NRRL B3411, and produce neutral proteases and amylases on a level about comparable to their alkaline protease production. Generally, the preferred enzymes are active proteolytic enzymes, with the most preferred being subtilisin A for use in non-dialyzer applications, e.g., endoscope and other semicritical medical devices. A particularly preferred commercial subtilisin A product is Alcalase® (Novo Nordisk Biochem North America, Inc., Franklinton, N.C.), available in granular as well as liquid product varieties. A particularly preferred variety of Alcalase® is a liquid concentrate known as Alcalase® 2.5 L, having a specific enzyme activity of 2.5 Anson units (A.U.) per gram. Alcalase® 2.5 L has a density of 1.056 g/ml, therefore the enzyme activity of Alcalase® 2.5 L can also be expressed as 2.64 A.U./ml. Other preferred enzymes available from the same source for non-dialyzer applications are Savinase®, a serine protease of the subtilisin class which is produced by submerged fermentation of a genetically modified alkalophilic species of Bacillus, Durazyme® 16.0 L, Type EX, a first generation protein-engineered variant of Savinase®, and Everlase®, a second generation protein-engineered variant of Savinase®.

Yet another preferred enzyme available from the same source for selected non-dialyzer applications is Neutrase®, a bacterial protease produced by a selected strain of *B. amyloliquefaciens*. Neutrase® contains only the neutral part of *B. amyloliquefaciens* proteases, whereas most other commercial preparations also contain the alkaline protease. Neutrase® is a zinc metalloprotease which is stabilized with $Ca^{2+}$ and consequently inhibited by EDTA. Neutrase® can be used for selected applications requiring a more neutral pH, as it has optimal activity between pH 5.5–7.0. Neutrase® has limited application as it is 100% inactivated in a solution containing $0.2\%^{w/v}$ PAA and $1.08\%^{w/v}$ $H_2O_2$. It is also inactivated by zinc and calcium chelating agents. A particularly preferred Neutrase® raw material is designated Neutrase® 0.5 L. The specific enzyme activity of Neutrase® 0.5 L is 0.5 A.U./gram, with a solution density of 1.226 g/ml.

Human enzymes from the serine protease class at a neutral or alkaline pH are preferred for kidney dialyzer applications. The reason for this is that the preferred human enzymes will not provoke an immune response if they enter the circulatory system in small amounts arising from desorption from the dialyzer fibers following the final rinsing step employed just prior to dialyzer use. Human trypsin and chymotrypsin are examples of suitable human enzymes for use at a neutral or alkaline pH. Enzymes such as recombinant human tissue plasminogen activator, anisoylated plasminogen streptokinase activator complex (APSAC; anistreplase), streptokinase and urokinase can also be used for kidney dialyzer applications. Additionally, preferred non-human enzymes for kidney dialyzer applications are enzymes which will not provoke an immune response because they have little to no interaction or binding with the dialyzer fibers, resulting in an insufficient amount of material desorbing from the fibers into the blood during dialysis to provoke an immune response. Enzyme interaction with dialyzer surfaces such as fibers can be measured with classical enzyme-substrate assays which can detect bound or desorbed active enzyme. A preferred substrate for use with a serine protease for this purpose is benzoylarginine ethyl ester (BAEE). The ethanol which is produced can be detected in very small amounts using gas chromatography. Total protein analyses can also be performed on dialyzer materials, provided that non-enzyme protein, if present, can be subtracted from the total.

Acid-acting enzymes are useful when it is desirable not to change the pH of an acid stabilized disinfecting solution such as acid stabilized peracetic acid (PAA)—$H_2O_2$. This situation may arise when a more alkaline pH for either of the latter solutions may be detrimental to the biocompatibility of the device or the shelf stability of the solution. $H_2O_2$—PAA solutions are typically stabilized between pH 1.9–3 to achieve a reasonable shelf-life of one to two years. Alternatively, it may be desirable to avoid adding a large amount of alkaline buffer due to buffer solubility limitations in a liquid enzyme formula. Thus, preferably, the acid-acting enzymes are effective between about pH 2–5. Specific examples of acid-acting enzymes which may be employed in the present invention include pepsins such as penicillopepsin from *Penicillium janthinellum,* gastricsin, chymosin (rennin), Cathepsin D, genetically engineered enzymes such as subtilisins with acid pH activity profiles, fungal acid proteases such as aspergillopeptidase A from *Aspergillus saitoi* and the like, acid-acting enzymes disclosed in U.S. Pat. No. 5,630,884, which is expressly incorporated herein by reference in its entirety, and mixtures thereof. Two additional acid-acting enzymes designated NS16009 and NS16010 (Novo Nordisk) are acid endoproteases from *A. niger var. aculeatus.* Acid-acting enzymes are also useful for kidney dialyzer reprocessing applications because of the need to minimize exposure to any residual active enzyme which may desorb from the dialyzer during use. In this situation, the desorbed enzyme would be exposed to the physiological pH of the circulating blood and thus would inherently be inactivated by the pH 7.45 environment. Additionally, an acid-acting enzyme in combination with an acid peroxide-containing disinfectant will not result in oxygen gas formation as occurs with neutral or alkaline pH, which can burst dialyzer fibers due to pressure build-up. A human acid-acting enzyme such as human pepsin or pepsinogen, the precursor of pepsin, would be most preferred for dialyzer applications.

While proteolytic enzymes are preferably utilized, it is also preferred to utilize a proteolytic enzyme in combination with one or more enzymes from the amylase, cellulase or lipase classes, especially for non-dialyzer applications. The use of an amylase along with a protease is particularly preferred. Preferred commercial amylases from Novo are DuraMyl™ and Termamyl® 300L. DuraMyl™ is a protein-engineered alpha-amylase produced by submerged fermentation of a genetically modified species of Bacillus. Termamy® 300L is an alpha-amylase produced by a selected strain of *Bacillus licheniformis*. Both amylases are endoamylases which hydrolyze 1,4-alpha-glycosidic linkages in amylase and amylopectin. Starch is therefore rapidly broken down to soluble dextrins and oligosaccharides. Both enzymes may be used in alkaline, neutral or acidic formulas. Other enzymes which can be utilized, particularly in combination with a protease include cellulases such as Celluzyme® and lipases such as Lipolase™ and Lipolase™ Ultra (all from Novo).

Methods for enzyme identification, separation and purification are well established. Many techniques exist in the general scientific literature for the isolation and identification of enzymes, including enzymes having proteolytic and mixed proteolytic/amylolytic or proteolytic/lipolytic activity. The enzymes contemplated by the present invention can be readily obtained by known techniques from plant, animal or microbial sources.

With the advent of recombinant DNA techniques, new sources and types of proteolytic enzymes have become available. Such enzymes, as well as enzymes produced through a combination of recombinant DNA or site-directed mutagenesis techniques with chemical modifications, should be considered to fall within the scope of this invention so long as they meet the criteria set forth herein. See Japanese laid open application No. J6 0030-685 (production of proteases by recombinant DNA from *Bacillus subtilis*), International Patent Application No. PCT/DK94/00274 and International Patent Application No. PCT/DK91/00103 (production of chemically-modified proteases by a combination of recombinant DNA or site-directed mutagenesis, such proteases being incorporated herein by reference). Additionally, native or wild-type enzymes which are subsequently chemically modified should also be considered to fall within the scope of this invention so long as they meet the criteria set forth herein.

Effective and Efficacious Amounts

The present invention generally employs an effective and efficacious amount of enzyme to clean the device or instrument, e.g., medical devices such as endoscopes or kidney dialyzers. An effective and efficacious amount is that which (1) removes, in a reasonable time a substantial portion of the proteinaceous or other deposits which occur during the use of the medical device, (2) does not decrease the efficacy of the decontaminating agent(s) when combined with the latter agent(s) in the working solution, and (3) allows the decontaminating agent(s) to achieve the standards, e.g., high-level disinfection and sterilization, required for the reprocessing of the particular device or instrument.

The precise amount of enzyme required to produce an effective and efficacious cleaner will depend on several factors including enzyme activity and purity, the amount of proteinaceous and other matter deposited, the desired soaking period and temperature, the nature and concentration of the decontaminating agent(s), the specific medical device or instrument, the delivery form of the enzyme and its related shelf stability, the presence of surfactants and other solution components known to enhance the activity of the particular enzyme, as well as other known factors.

Activity

The precise amount of enzyme used by weight will vary with the purity and specific activity of the enzyme, normally expressed as Anson Units per gram, (A.U./g), which can vary on a lot-by-lot basis. Additionally, the expected enzyme activity loss during shelf storage and during the solution reuse period, if any, must be considered. It is standard practice with proteolytic enzyme cleaning products to expect about a 40–50% enzyme activity loss during a two year shelf-life and to properly plan for this by formulating with a higher level of enzyme than is needed. Activity losses during the reuse period may also be about 50%. The temperature of the combined cleaning and decontaminating solution is also a critical determinant of the amount of enzyme to utilize, as is the regimen soak time. The regimen soak time for reprocessing endoscopes and other semicritical medical devices utilizing the present invention is generally between about 10–30 min, preferably between about 10–20 min although shorter soak times can be employed for all applications and longer soak times for kidney dialyzers. The regimen soak time for reprocessing kidney dialyzers can be as short as 1 min with ultrasonic energy input, to 10–20 min and as long as or longer than 43 hours, which is almost as long as the 48 hour interdialysis period. Generally, the longer the soak time, the less enzyme is necessary for cleaning if activity losses are the same. Enzyme activity loss from exposure to the decontaminant is greater with longer regimen soak times. Thus, these two effects need to be balanced in the final enzyme formula.

If the enzyme cleaning component is formulated as a separate solution from the decontaminating component, such that the two must be mixed prior to use, consideration must be made for dilution of the enzyme. Current stand-alone (i.e., no decontaminant) proteolytic enzymatic pre-cleaners for semicritical medical devices utilize generally between about 0.0012 and 0.0031 A.U./ml final soak volume following a dilution of 1 ounce into 1 gallon (total volume 129 ounces). Thus, the current stand-alone enzymatic pre-cleaners are concentrates with enzyme activity generally between 0.154–0.397 A.U./ml. The diluted solutions are designed for the most part to be used for 10 min with warm water at 50° C. In contrast, the combined cleaning and decontaminating solutions of the present invention are designed to be used primarily for about 10–30 min at 20° C., with a preferred soak time of 20 min for endoscope reprocessing. Since there is a nominal eight-times rate enhancement of enzyme activity at 50° C. over 20° C., eight times the amount of enzyme would be necessary at 20° C. to achieve the same cleaning. Also, half the enzyme amount can generally achieve the same cleaning in twice the soak time (20 min versus 10 min).

Surprisingly, the combined cleaning and decontaminating solutions of the present invention achieve significantly greater cleaning per unit of enzyme than prior stand-alone enzyme solutions, therefore the aforementioned amounts of enzyme can be reduced. Taking under consideration the enhancement of cleaning, which can in many cases make up for expected storage losses, the combined cleaning and decontaminating solutions of the present invention should contain between about 0.0048 (4×0.0012) and 0.0124 (4×0.0031) A.U./ml of final working solution to ensure that the same cleaning effect is achieved for semicritical medical devices. This activity range is multiplied by 129 in the case wherein the enzyme is kept separate from the decontaminant prior to use and is diluted 1 ounce into 1 gallon (128 ounces) to achieve a final working solution. Thus, the enzyme activity range for the separate enzyme concentrate would be about 0.619–1.600 A.U./ml. Similar considerations need to be taken in determining the appropriate amount of enzyme to be utilized for kidney dialyzer reprocessing.

Taking all factors under consideration, the final working solution should contain sufficient proteolytic enzyme to provide between about 0.00001–10 A.U./ml, preferably between about 0.001–0.10 A.U./ml, and more preferably between about 0.0048–0.0124 A.U./ml soak volume.

Where an amylase enzyme is employed, similar considerations need to be taken in determining the appropriate amount of enzyme. Thus, the recommended amounts of amylase enzyme to utilize are the same, however they are expressed in Kilo Novo units/ml, wherein for every 2.5 A.U., 300 Kilo Novo units are substituted. Thus, the aforementioned recommended range limits for proteolytic enzymes are multiplied by (300/2.5)=120. Therefore, the more preferred proteolytic enzyme range of 0.0048–0.0124 A.U./ml is translated to 0.58–1.49 Kilo Novo units/ml for an amylase enzyme. One Kilo Novo alpha-amylase unit is the amount of enzyme which breaks down 5.26 g starch/h in Novo's standard analytical method AF-9 for the determination of alpha-amylase. Also, as previously taught, both types of enzyme may be employed separately, together or combined with another type of enzyme. Where both a proteolytic and amylolytic enzyme are employed together, each is recommended to be used within their above respective ranges.

pH

Enzyme activity is pH dependent and for any given enzyme, there is an optimum pH range as determined by techniques known to one skilled in the art. It is preferred, but not required, to manipulate the working solution to an optimum pH range for a given enzyme. Generally, it is preferred that the enzyme be selected to have activity between pH 6–9, even more preferably between pH 6.5–8.5, and most preferably between pH 7–8.5. These pH ranges avoid acidic solutions which can be corrosive to metal-containing devices and instruments. Strongly alkaline solutions >pH 9 are also generally undesirable as they impart chemical instability to per-compound based disinfectants such as $H_2O_2$ plus PAA. This chemical instability may also cause a too-rapid breakdown of medical devices. One of the preferred commercially available proteolytic enzymes for endoscope cleaning applications, Alcalase® 2.5 L, has an optimal activity profile between about pH 6–12, with a peak cleaning activity between about pH 8–8.5. A preferred amylase enzyme such as Duramyl™ has high activity between about pH 5–9 and optimal activity between about pH 6–7, whereas another preferred amylase enzyme, Termamyl®, has high activity between about pH 5–9 and optimal activity between about pH 6–8. Also preferred are enzymes that have activity between pH 1.5–3.0, where most per-compounds are stable. These compositions would also preferably include a metal corrosion inhibitor for non-dialyzer applications.

Formulation

The enzyme component may be employed in liquid or solid form such as tablets, pills, capsules, granules and the like which is introduced into the liquid medium. Due to the time constraints for medical device reprocessing which currently exist to control labor costs and maximize profits, it is desirable to utilize a delivery form for the enzyme which is most efficient for the user of the reprocessing system. In this context, a liquid enzyme concentrate which can be rapidly diluted into a high-level decontaminating solution is most preferred, especially for endoscope reprocessing with soak times as short as 20 min. The disinfecting solution in this context can be a concentrate itself, wherein distilled, pyrogen-free, microbe-free or tap water would also be added before, at or after the time of addition of the enzyme solution to achieve the final use-dilution concentration of the combined enzyme and decontaminant solution. Alternatively, enzymes may be formulated in rapidly dissolving effervescent granules to minimize reprocessing time. Effervescing agents are typically employed when the enzyme component is provided in solid form. Examples of suitable effervescing agents include tartaric or citric acid used in combination with a suitable alkali metal salt such as sodium carbonate. In addition, binders, lubricants, carriers, and other excipients normally used in producing tablets may be used when enzyme component-containing tablets are employed. The decontaminating per-compound may also be included in the enzyme solid dose form such as a tablet.

Stabilizers

The shelf-life stability of enzymes useful in the present invention can be achieved or improved with standard methods such as adding calcium ions for subtilisin in a liquid formulation or producing a liquid formulation of low water content. One way of reducing water in the formulation is to use propylene glycol, other glycols, as well as other polyols such as various sugars, e.g., sorbitol. Concentrations of glycols between $20\%^{w/v}$–$70\%^{w/v}$ are preferred, although lower or higher concentrations may be employed. Other conventional means for stabilizing a liquid enzyme formulation can also be employed. The aforementioned considerations do not generally apply to solid state enzyme formulations, the latter which can be stabilized by conventional means, e.g., using very dry raw materials or other known methods.

Decontaminating Agents

The disinfecting or sterilizing agent(s), collectively termed decontaminating agents, may be any of one or more per-compounds which produce active oxygen in solution and which can achieve high- or intermediate-level disinfection or sterilization. Examples of such compounds include inorganic peroxides, peracids (which exist in equilibrium with a certain amount of $H_2O_2$) such as PAA and $H_2O_2$ plus PAA, with PAA and mixtures of $H_2O_2$ and PAA being preferred. PAA or other peracids, alone or in combination, may also be used. Peracids produced from $C_1$–$C_4$ mono or dicarboxylic acids, such as performic acid and perpropionic acid may be used. Peracids produced from carboxylic acids with linear, saturated or unsaturated hydrocarbon chains having 5–20 carbon atoms may also be used. Alkali metal persulfates, alkali metal carbonate peroxide, diperisophthalic acid, peroxydiphosphate salts and sodium aluminum aminohydroperoxide are examples of compounds which can also be used in combination with one or more peracids or one or more solid peracid precursors, such as tetraacetylethylenediamine (TAED) or acetylsalicylic acid. Collectively, these compounds are all per-compound oxidant-based anti-microbial agents.

Existing high-level disinfecting solutions such as the $7.5\%^{w/w}$ solution of $H_2O_2$ (and an unspecified peracid) marketed as Sporox® (Reckitt and Colman, Montvale, N.J.)

and the mixture of 1.0%$^{w/w}$ H$_2$O$_2$ and 0.08%$^{w/w}$ PAA marketed as Cidex PA® (Johnson and Johnson, Irvine, Calif.) or Peract 20® (Minntech Corp, Minneapolis, Minn.) also may be utilized in the compositions and methods of the present invention. Renalin® Dialyzer Reprocessing Concentrate (Renal Systems Division, Minntech Corp.) may also be utilized.

Additionally, hydrogen peroxide-peracid compositions disclosed in U.S. Pat. No. 4,518,585, (which inherently generate a peracid), which is expressly incorporated herein by reference in its entirety, may be employed in the present invention provided they meet the decontamination standards herein.

Effective and Efficacious Amounts

The identity, concentration and contact time of the selected agent(s) will vary depending on the extent of decontamination; that is, whether high- or intermediate-level disinfection or sterilization is desired. In many applications, only high-level disinfection is sought. The disinfecting or sterilizing contact time is also a function of the concentration of the decontaminating agent(s) employed. Hence, the contact time or the concentration(s) of the disinfecting agent(s) may be adjusted accordingly. As an example, Sporox® has a high-level disinfection time of 30 minutes at 20° C. and a sterilization time of 6 h at 20° C. Cidex PA® has a high-level disinfection time of 25 min at 20° C. and a sterilization time of 8 h at 20° C. The identity and concentration of selected decontaminating agents is also dependent upon the type of device requiring cleaning and decontamination. Devices containing metals, especially soft metals, require non-corrosive solutions. Peracetic acid solutions which minimize acetic acid contant will minimize metal corrosion. Given the known reaction between hydrogen peroxide and acetic acid to produce peracetic acid and the equilibrium relationship between the three molecules, it is desireable to maximize the concentration of hydrogen peroxide and minimize the concentration of acetic acid to produce a desired amount of peracetic acid for a minimally corrosive solution. For example, a hydrogen peroxide concentration of about 7.5%$^{w/w}$ in combination with varying amounts of acetic acid is optimal for producing varying amounts of peracetic acid in the less hazardous concentration range of less than 8.0%$^{w/w}$ H$_2$O$_2$. Also, since in decontaminating agent solutions containing both hydrogen peroxide and peracetic acid, the sporicidal activity is contributed to significantly by hydrogen peroxide, it is often preferable to maximize the concentration of hydrogen peroxide as much as possible. Another factor is the inherent instability of both peracetic acid and hydrogen peroxide. Moreover, peracetic acid stability is dependent upon hydrogen peroxide stability. If hydrogen peroxide is neutralized or decays, the peracetic acid will rapidly decay to acetic acid and hydrogen peroxide owing to the equilibrium relationship noted above. Thus there is a need for stabilization of hydrogen peroxide in such solutions.

A single peroxide concentration cannot apply to all peroxides as the percentage of active oxygen varies substantially among peroxides. The preferred concentration range for H$_2$O$_2$ in combination with a peracid such as peracetic acid is between about 3.0–8.0%$^{w/w}$, with a more preferred range between about 6.0–8.0%$^{w/w}$. However, concentrations ≧8.0%$^{w/w}$ are generally undesirable as concentrations of H$_2$O$_2$ between 8.0–16%$^{w/w}$ are classified by the United States Department of Transportation as significantly more hazardous than lower concentrations and must therefore be handled accordingly, imposing costlier shipping requirements. Concentrations of H$_2$O$_2$ <6.0%$^{w/w}$ are less preferred since these require significantly longer high-level disinfection and sterilization times. Lower or higher concentrations of H$_2$O$_2$ may be employed in combination with a peracid from about 0.5–50%$^{w/w}$.

The preferred concentration range for PAA is between about 0.05–0.30%$^{w/w}$, with an even more preferred concentration range between about 0.08–0.22%$^{w/w}$. Concentrations higher than about 0.30%$^{w/w}$ are generally undesirable as they are too corrosive to adhesives and other components of devices. However, concentrations as high as 5% can be employed provided an appropriate level of anticorrosive agent(s) is also present. PAA at concentrations <0.05%$^{w/w}$ has not been shown to be an effective high-level disinfectant or sterilant with contact times of 30 minutes or less, with 0.05%$^{w/w}$ PAA stated as being the minimum effective concentration for high-level disinfection at 25 minutes contact at 20° C.

The appropriate concentrations of any given peroxide will be a matter to be determined through routine laboratory testing as known to one skilled in the art.

Stabilizers

Decontaminating agents such as PAA or mixtures of H$_2$O$_2$ and PAA are inherently unstable above pH 4–5, rapidly decaying to water and oxygen in the case of H$_2$O$_2$ and additionally to acetic acid in the case of PAA. Thus, such solutions are pH stabilized, preferably between about pH 1–3, more preferably between about pH 1.5–3, and even more preferably between about pH 1.6–2.0. This is achieved with an acidic compound such as an inorganic or organic acid, typically at a concentration between 0.001–10%. Additionally, transition metals such as iron, manganese and copper also destabilize peroxides. Such metal-induced destabilization can be prevented with sequestrants such as hydroxy-ethylidene diphosphonic acid (Dequest 2010™, Monsanto Co.), or with the use of conventional chelating agents. Preferred concentrations for Dequest 2010™ are between 0.10 and 1.0%$^{w/v}$. Other conventional means of stabilizing peroxides can also be employed, such as nitrilotrismethyl-, methyl- and other phosphonic acids and nonionic surfactant stabilizers.

Formulation

The decontaminating agent may be employed in liquid or solid form. Solid forms include tablets, pills, capsules, granules and the like which are introduced into a liquid diluent such as water. Due to the current time constraints for medical device reprocessing to control labor costs and maximize profits, it is desirable to utilize a delivery form for the decontaminant which is most efficient for the user of the reprocessing system. In this context a liquid form, either concentrated or already diluted to its final use dilution, is most preferred. If the disinfecting agent is utilized in a liquid concentrate designed to be diluted with tap water to its final use-dilution prior to use, it needs to be compatible with water hardness cations (CA$^{2+}$ and Mg$^{2+}$) up to between about 500 and 1000 ppm CaCO$_3$ equivalence, and ideally between about 800 and 1000 ppm. Compatibility in this context includes the performance that the concentrate will not form a precipitate with calcium or magnesium or other entities in the tap water. This can be achieved by avoiding the use of formulation excipients that will form precipitates with calcium or magnesium or alternatively, by using sufficient chelators to complex calcium and magnesium. These same considerations apply to enzyme concentrates which may be mixed with tap water. Lastly, other forms of purified water such as sterile water may also be utilized to dilute a concentrated disinfectant. Alternatively, decontaminating agents may be formulated in rapidly dissolving effervescent granules to minimize reprocessing time.

Additional Components

Buffering agents, chelating agents, anticorrosive agents, surfactants, antifoam agents, soil antiredeposition agents, preservatives, tonicity adjusting agents, indicator dyes, fragrances and the like can be employed in the composition of the invention.

Buffering Agents

A buffer should be added to a separate enzyme formulation to maximize the enzyme activity if the pH of the combined decontaminating and cleaning solution is designed to be different than that of decontaminating formulation alone. Additionally, each device, when added to the combined enzyme and disinfectant solution, may carry over an amount of rinse water or other rinse liquid into the combined solution, adversely changing its pH and/or buffer capacity. A neutral or alkaline buffer used to provide a proper working pH for a corresponding neutral or alkaline enzyme can also serve to buffer the combined enzyme and disinfectant solution so that it can be re-used to clean and disinfect a plurality of devices over one or more days.

Usually, a large amount of buffer is required in the enzyme formulation so that the pH of the very acidic $H_2O_2$ and/or PAA solutions at which the latter are stable can be enhanced with much smaller quantities of enzyme formulation (i.e., 1 gallon PAA/$H_2O_2$:1 ounce liquid enzyme formulation is a preferred volume ratio). However, many buffers are either insoluble or unstable at the required high concentrations in liquid enzyme formulations which contain a large amount of organic solvents, such as propylene glycol, to stabilize the enzyme to achieve a reasonable shelf life. For example, buffers disclosed in the prior art such as 0.5–1 M phosphate buffer and borate buffer solutions in the presence of 23%$^{w/v}$ propylene glycol, 15%$^{w/v}$ Macon 10 and 10.7%$^{w/v}$ Alcalase® form two liquid phases and a precipitate, respectively. It was discovered that large amounts of buffering agents can be dissolved in low water content enzyme solutions if proper hydrophobicity of the buffering agent molecules is carefully selected. If such a buffering agent in a required amount with high hydrophobicity is still not soluble, one can use organic counter ions with sufficient hydrophobicity to replace the lower hydrophobicity counter ions. Examples of qualified buffering agents are 2-amino-2-hydroxymethyl-1,3-propanediol/acetic acid, 2-amino-2-methyl-1-propanol, ethanolamine/lactic acid and triethanolamine (TEA). High tris(hydroxymethyl) aminomethane (Tris) buffer concentrations sometimes can cause the solution to be unstable if the pH of the mixed enzyme solutions is adjusted with inorganic acid, thus the Tris inorganic acid buffer compositions taught in the aforementioned U.S. Pat. No. 5,356,555 are unsuitable for concentrated enzyme solutions. Tris is preferably paired with an organic counter ion such as acetate from acetic acid or borate from boric acid. However, inorganic or combined inorganic-organic buffers can be used in the enzyme formulation if the enzyme solution either does not require its own strong buffer (e.g., in the case wherein an acid-acting enzyme is employed with an acid per-compound) or in the case wherein a solid enzyme formula is used which does not require a polyol enzyme stabilizing agent. Inorganic or organic buffers can be used as part of per-compound formulas, whether the latter are solids, concentrated solutions or solutions already diluted to their final working concentration. Examples of suitable buffers for use in the present invention are also presented in Tables 7c and 14a. In general, a concentration of buffer between about 2 mM and about 2 M can be used in compositions of the present invention. Preferably, between about 0.25 M and 1.5 M of completely organic buffer is used in an enzyme solution concentrate designed to be diluted 129-fold with a liquid disinfectant. However, lower or higher concentrations can be used.

Chelating Agents

Transition metal ions such as Fe(III), Fe(II), Cu(II) and Ni(II) usually exist in oxidant disinfecting and sterilizing solutions as the result of metal corrosion occurring in the process of instrument disinfection and sterilization. Fe(III) and Fe(II) are also introduced into a disinfecting and sterilizing solution by blood remaining on a medical instrument to be disinfected or sterilized. It is known that trace levels of transition metals can participate in the metal-catalyzed Haber-Weiss reaction or superoxide-driven Fenton reaction, which causes $H_2O_2$ to decompose into $O_2$ (Buettner, Radiation Research 145, 532–541 (1996)). Also, the destabilization of $H_2O_2$ will cause the destabilization of PAA or other peracids derived from $H_2O_2$ when the two (e.g., $H_2O_2$ and PAA) are combined. It is, therefore, necessary to sufficiently stabilize $H_2O_2$ in reusable oxidant-based disinfecting or sterilizing solutions.

Chelating agents have been used extensively to study the catalytic nature of metals in free radical oxidative processes. It was shown in the literature that EDTA enhances the reactivity of Fe(III) toward superoxide, forming Fe(II) (Buettner, Photochem. Photobiol. 28, 693–695 (1978)), and results in an accelerated $H_2O_2$ degradation process. It was also shown that diethylenetriamine pentaacetic acid (DETAPAC) drastically slows the reactivity of Fe(III) toward superoxide forming Fe(II). Regardless of the opposite roles of chelating agents in stabilizing or destabilizing $H_2O_2$ as described in the prior art, we discovered unexpectedly that some chelating agents such as EDTA which are reported in the literature to accelerate the Fe(III) conversion to Fe(II) superoxide-driven Fenton reaction can actually stabilize $H_2O_2$ when their concentrations are low. For such a chelating agent-$H_2O_2$-transition metal system there exists a maximum chelating agent concentration at which $H_2O_2$ in a disinfecting or sterilizing solution can reach a maximum stability. Chelating agents such as EDTA, DETAPAC and similar compounds may be employed in an amount at which the stability of $H_2O_2$ is at maximum. It has been found the Na$_2$EDTA concentrations in the solution between about 0.05%$^{w/v}$ and 0.35%$^{w/v}$ are preferred. The optimal amount of chelating agent or agents can be determined with the methods and teachings herein.

Anticorrosive Agents

Copper or brass corrosion inhibitors such as triazoles, azoles, benzoates, or five-membered ring compounds may be added to the decontaminant formula, as long as they do not interfere with the activity of the enzyme or disinfectant. A preferred corrosion inhibitor within this class is 1,2,3-benzotriazole, at a concentration between about 0.10 and 1.0%$^{w/v}$. Commonly known corrosion inhibitors for aluminum and stainless steel such as borates, phosphates and tungstates may also be included as long as they do not interfere with the activity of the enzyme or disinfectant. Preferably, the corrosion inhibitors do not form a deeply colored complex in the final solution, which would be unacceptable to the user. For example, it was found that the common corrosion inhibitor molybdate forms an unacceptably dark solution at pH 8.5. Typical concentrations for corrosion inhibitors are between about 0.001%–10%$^{w/v}$.

Surfactants

The surface of a used medical instrument usually forms hydrophobic domains as the result of surface adsorption of the organic components in body fluid. Thus, a surfactant may be added to the decontaminant solution and/or to the cleaning solution as another cleaning agent. A surfactant can effectively remove most organic soils from the surface of a used instrument, and can stabilize the organic soils in the solution through the formation of emulsions or solubilized micelles. Another function of surfactants in a disinfecting/sterilizing solution is to solubilize the large molecular weight enzyme-hydrolyzed proteins and therefore to prevent them from forming precipitates.

The choice of surfactants significantly influences the rate of denaturation of enzymes. Anionic surfactants are generally denaturing, whereas nonionic surfactants are neutral or even stabilizing to enzymes. Therefore the ratio of anionic:nonionic surfactants should not be too high, preferably below 1, and most preferably below 0.5.

On the other hand, $O_2$ gas is constantly generated in $H_2O_2$ and/or PAA decontaminant solutions due to either disinfection or solution instability in the presence of organic soils. $O_2$ gas bubbles can anchor onto the hydrophobic domain surface of the instrument, which can effectively prevent the decontaminant solution from contacting the instrument surface and consequently defy the disinfection/sterilization action of the solution. Thus, wetting agents such as nonionic or anionic surfactants may be added to minimize $O_2$ gas bubbles from adhering to the used instrument surface.

Surfactants which are incorporated directly into high-level disinfecting solutions such as 7.5% $H_2O_2$ in combination with PAA should be stable in the solution and not interfere with disinfection. Such surfactants can be selected with conventional screening techniques. Makon 10 and Makon NF-12 are examples of suitable nonionic surfactants.

A preferred concentration range for surfactants in the final working solution is $0.001-1.0\%^{w/v}$, with an even more preferred range of $0.01-0.25\%^{w/v}$. Lower or higher concentrations may be used, however, depending upon the expected level of soils that need to be solubilized.

Antifoam Agents

Antifoam agents or defoamers may be added to either the cleaning component or the disinfectant component. Antifoam agents prevent excessive foam formation arising from agitation of any surfactant in the solution during dilution of the cleaning or decontaminant formula or during reprocessing of the device, e.g., during manual brushing of the narrow channels and other surfaces of an endoscope during the combined simultaneous cleaning and disinfecting step. Antifoam agents such as dimethyl polysiloxane (Antifoam C) (Dow Corning Corp., Midland, Mich.) may be utilized at a concentration <0.26 ml/liter or between about 0.005 and $0.05\%^{w/v}$ in a concentrate designed to be diluted 1:128 with water. The particular antifoam agent employed will depend upon the amount and type of surfactant utilized.

Soil Antiredeposition Agents

Soil antiredeposition agents or antisoils may be added to either the cleaning or disinfectant component to prevent redeposition of removed soil onto the cleaned device such as a medical device. Such agents are preferably used with a reusable medical device reprocessing system, which will be exposed to more soil than a single-use system. Thus, such agents are preferably used with reprocessing of multiple endoscopes in the same solution and are generally not useful for reprocessing kidney dialyzers with single-use solutions. Agents such as polyacrylic acid, carboxymethylcellulose and polyvinylpyrrolidone may be employed in conventional amounts as antiredeposition agents.

Preservatives

Preservatives may be added to the formulas of the present invention, particularly to a separate liquid enzyme formula to preserve the solution against contamination from microorganisms such as bacteria, yeasts and fungi. Conventional preservatives such as thimerosal may be employed, as long as they do not interfere with the performance of the cleaning and decontaminating system. EDTA may be employed, with a preferred concentration of $0.05\%-0.10\%^{w/v}$ in the formula requiring preservation. EDTA is preferably used in combination with sorbic acid or potassium sorbate, the latter at a concentration of $0.10-0.20\%^{w/v}$. Other common preservatives such as benzalkonium chloride (about $0.0044-0.0100\%^{w/v}$) or methyl paraben (methyl 4-hydroxy benzoate about $0.1\%^{w/v}$) may be employed. Other parabens such as benzyl-4-hydroxybenzoate, ethyl-4-hydroxybenzoate, propyl-4-hydroxybenzoate and butyl-4-hydroxybenzoate can also be employed as preservatives. Dowicide® 1 (Dow Chemical USA) is another example of an acceptable preservative. Dowicide® 1 is o-phenylphenol and is typically used at a concentration of $0.10-0.20\%^{w/v}$. Preservatives may be used alone or in combination.

Tonicity Adjusting Agents

A tonicity adjusting agent or agents may be incorporated into either the cleaning component or decontaminating component to adjust the osmotic value of the formula or final cleaning and decontaminating solution to achieve greater chemical stability or to optimize another performance parameter. Tonicity adjusting agents are more important in some cases for kidney dialyzer reprocessing applications, since the dialyzers may contain dialysis fibers or membranes which respond to changes in solution osmolarity, changing their membrane characteristics and hence their filtration characteristics. Conventional tonicity adjusting agents such as simple electrolytes, e.g., sodium and potassium chloride, etc. and other non-ionic agents such as simple sugars, e.g., glucose, etc. may be employed.

Indicator Dyes

Indicator dyes can be added to enhance user compliance with the reprocessing steps and additionally to serve as an indicator of completion of the required decontamination soak time if desired. The dyes may be added to either the separate cleaning formula, a separate decontaminant formula, both separate formulas or to a combined cleaning plus decontaminant formula to differentiate the formula from water or other reprocessing solutions. An indicator dye such as FD&C blue dye #1 may be used for both purposes.

The dye is added to the formula at a concentration sufficient either to produce the desired color or to provide an indication of completion of decontamination soak time through a controlled redox reaction with the oxidant-based decontaminant. The latter reaction proceeds through a basic dye-bleaching mechanism, wherein the initially colored dye is bleached to a new color or to a colorless state with one of the components of an oxidant-based decontaminant, such as $H_2O_2$, at a defined rate which can be controlled through conventional control of dye-bleaching reactions. FD&C blue dye #1 or other dyes such as Pyla-Cert Mx3 (Grass Green) or FD&C green dye #1 are typically used at a concentration of between about 0.001 and $0.010\%^{w/v}$, preferably $0.004\%^{w/v}$ in an enzyme concentrate formula designed to be diluted 1:128 in water.

Indicators, which are colorants which indicate the presence or absence of $H_2O_2$ or PAA or other peroxides may also be incorporated into these formulations.

Fragrances

Fragrances such as peppermint oil may be added to mask disagreeable odors or to create an agreeable fragrance. Fragrances may be added to either the separate cleaning formula, a separate decontaminant formula, both separate formulas or to a combined cleaning plus decontaminating formula. A typical concentration for peppermint oil is 0.204 ml/l in an enzyme concentrate formula designed to be diluted 1:128 in water.

Concentrations between about 0.01 and 0.04%$^{w/v}$ are preferred.

Method

In use, a solution of per-compound and enzyme is prepared and one or more devices such as a medical device is contacted with this solution, preferably by immersion in the solution. The device may first be treated to remove loosely adhering soil, then contacted with this solution. The device is maintained in contact with this solution long enough so that substantially all protein and other soils are removed from the device surfaces and the device is disinfected or sterilized. The solution may then be removed from the device.

The sequence of combining the essential components for the solution which contacts the device will vary with the physical characteristics of the component employed, but the order of addition is not critical to the practice of this invention.

There is no particularly preferred form for manufacturing these materials. The two essential components, i.e. the cleaning and decontaminating components, may be formulated as separate components in dry or aqueous form, may be combined in a single solid form, or either one may be in a dry form while the other is an aqueous solution.

Other energy input may be employed to potentiate the solution's cleaning and decontaminating effect. For example, ultrasonic devices are known to potentiate the speed at which enzymes work in such circumstances in cleaning and may be employed.

The practice of this invention is not to be limited by temperature except by those temperature extremes which would substantially inactivate the capability of the enzymes employed, as is known to one skilled in the art.

It is also contemplated that certain components may be separately prepared in a manner to effect the timed release of that component or to prevent interaction of the components during tablet, granule or powder preparation and subsequent storage. For example, in certain instances it may be appropriate to separately prepare the per-compound and the enzyme in a manner to prevent or reduce their interaction in a tableting or granulation process and upon subsequent storage thereafter.

In addition, solutions or powders may contain agents for detoxifying residual per-compound as part of the overall process of cleaning, decontaminating and ultimately removing residual per-compound. Enzymes which catalyze the conversion of per-compounds to oxygen and water can be included in these formulations to remove residual per-compound in anticipation of reinserting devices into the body. For example catalases, which are organic enzymes that catalyze the degradation of per-compounds, can be incorporated particularly into tablets, granules and powders, more particularly in a time-release form. Additionally, metals such as the heavy metal transition elements which catalyze the conversion of per-compound to oxygen and water can be included preferably in a powder, granule or tablet form, again preferably in some delayed release form to provide a method for reducing any residual per-compound remaining in the solution to a non-toxic level after a given time interval. The use of transition metal catalysts for decomposing peroxides in a disinfecting solution is disclosed in U.S. Pat. No. 3,912,451, which is expressly incorporated herein by reference in its entirety.

The compositions and methods of the present invention can also be utilized with existing or suitably modified medical device reprocessing machines and their associated per-compound disinfection chemistries, in addition to the manual methods previously described. The Steris® System 1™ Sterile Processing System and its associated per-compound chemistry (Steris Corp., Mentor, Ohio) for example, can be utilized with the compositions and methods of the present invention. The Steris® System 1™ and associated chemistry is disclosed in U.S. Pat. Nos. 4,731,222; 4,892,706; 5,037,623; 5,077,008 and 5,091,343; Canadian patent Nos 1,273,774; 1,321,137; 1,320,030; Japanese patent Nos 1,745,511; 1,852,815; Austrian EP 0,397,352; 0,322,310 and EP 0,232,170, all of which are incorporated herein by reference.

The Steris® System 1™ and associated chemistry can be utilized with the compositions and methods of the present invention with or without modifying any of the machine hardware or software components or sterilant chemistry package currently in use. The latter package is a two compartment cup for powdered reagents which interact in water to form an antimicrobial solution. The presently marketed chemistry package utilizes sodium perborate and acetylsalicylic acid as two powdered reagents in a two compartment cup. A cleaning enzyme of the present invention such as subtilisin-A in the form of Novo Alcalase® 2.5 L can be combined with either the sodium perborate or the acetylsalicylic acid. The enzyme may be additionally protected from premature inactivation by either the perborate or acetylsalicylic acid during storage and prior to use by utilizing a coated granulation enzyme formulation. Upon dissolution with water according to the above Steris® patents and in accordance with the present invention, the combined enzyme, perborate and acetylsalicylic acid solution will produce a solution of sodium metaborate, a high-level disinfecting amount of PAA, salicylic acid and subtilisin-A. This solution can be delivered to the medical device according to the current Steris® System1™ process wherein only a high-level disinfection step occurs over approximately a 12 min period at between about 43–48° C., however, with the composition and method of the present invention a simultaneous cleaning and disinfection step occurs over this same time period and at this same temperature. Following this step, the same machine processing steps would occur as without the enzyme, e.g., several rinsing cycles (the presently marketed instrument utilizes four rinsing cycles) and final processing steps. It is also possible to utilize other simultaneous cleaning and disinfection time intervals and temperatures, as long as the enzyme or enzymes utilized effect cleaning.

Preferred Compositions

The following are preferred compositions of the present invention, with applications, preferred delivery forms, components and concentration ranges:

Reusable Composition for Endoscope and Other Semi-critical Medical Device Reprocessing Aqueous solution of enzyme, to be dissolved 1 ounce into 1 gallon (128 ounces) of disinfecting agent solution.

| Functional Component | Raw Material | Concentration %$^{w/v}$ |
|---|---|---|
| Enzyme (protease) | Alcalase 2.5 L | 2.5–50.0 |
| Enzyme (amylase) | Termamyl 300L | 2.5–50.0 |
| Enzyme stabilizer | propylene glycol | 20–70 |
| pH buffer | Tris | 3.0–18.0 |
| Surfactant | Makon 10 | 5.0–30.0 |
| Antifoam | Antifoam C | 0.005–0.05 |
| Preservative | Dowicide 1 | 0.10–0.20 |

-continued

| Functional Component | Raw Material | Concentration %$^{w/v}$ |
|---|---|---|
| Indicator dye | FD&C Green Dye #1 | 0.001–0.010 |
| Fragrance | Peppermint Oil | 0.01–0.04 |
| Diluent | Water | q.s. to volume |

Aqueous solution of disinfecting agent

| Functional Component | Raw Material | Concentration %$^{w/v}$ |
|---|---|---|
| Disinfecting agent | hydrogen peroxide | 6.0–8.0 |
| Disinfecting agent | peracetic acid | 0.08–0.20 |
| Chelating agent | Na$_2$EDTA | 0.05–0.35 |
| H$_2$O$_2$ Stabilizer | Dequest 2010 | 0.10–1.0 |
| Buffer/H$_2$O$_2$ stabilizer | boric acid | 0.006–0.60 |
| Anticorrosive | 1,2,3-benzotriazole | 0.10–1.0 |
| Diluent | water | q.s. to volume |

In the above combined solution, the pH can be between 5–9. Another preferred reusable composition for endoscope and other semi-critical medical device reprocessing uses the same disinfecting solution as above along with the enzyme solution which follows:

| Functional Component | Raw Material | Concentration %$^{w/v}$ |
|---|---|---|
| Enzyme (protease) | pepsin (e.g., porcine) | 2.5.50.0 |
| Enzyme stabilizer | propylene glycol | 20–70 |
| Preservative | Dowicide 1 | 0.10–0.20 |
| Diluent | water | q.s. to volume |

In this system, the pH of the disinfecting solution can be between 1–3 where the disinfectants are stable and active and the pepsin is also active. The pH of the enzyme solution is also adjusted to between 1–3 with H$_3$PO$_4$ prior to adding it to the disinfectant solution. Thus, an additional buffer is not required to be added to the enzyme solution.

Another preferred composition for reprocessing dental instruments in an ultrasonic cleaning bath containing about 2000 ml water at 50° C. follows:

| Functional Component | Raw Material | Concentration %$^{w/v}$ |
|---|---|---|
| Enzyme (protease) | Everlase | 0.2003 |
| H$_2$O$_2$ source | Potassium monopersulfate | 1.009 |
| Peracetic acid precursor | Acetylsalicylic acid | 1.007 |
| Buffer | Na$_3$PO$_4$.12H$_2$O | 2.2003 |

In the above example, the H$_2$O$_2$ from the monopersulfate combines with the peracetic acid precursor to produce sufficient peracetic acid to decontaminate the instruments. Sodium perborate monohydrate at about 1%$^{w/v}$ can also be used as a source of hydrogen peroxide. Combinations of Na$_2$HPO$_4$ (0.12%$^{w/v}$) and NaH$_2$PO$_4$ (0.08%$^{w/v}$) can be used to buffer the solution at pH 7.5 if desired. Alternatively, an acid-acting protease can be utilized at a pH preferably around 3–3.5 together with a suitable buffer.

In this system, the pH of the disinfecting solution can be between 1–3 where the disinfectants are stable and active and the pepsin is also active. The pH of the enzyme solution is also adjusted to between 1–3 with H$_3$PO$_4$ prior to adding it to the disinfectant solution. Thus, an additional buffer is not required to be added to the enzyme solution.

Single Use Composition for Kidney Dialyzer Reprocessing

Enzyme tablet formula, to be dissolved 1 tablet into each 250 ml of disinfecting/sterilizing agent solution just prior to use (combined solution pH range 1–6):

| Functional Component | Raw Material | Concentration |
|---|---|---|
| Enzyme (protease) | Human Pepsin | 0.0008–0.0030 AU/ml* |
| Tablet filler | Di-Pac** | 80%$^{w/w}$/tablet |
| Tablet binder | Povidone, PVP k-30*** | 8.0%$^{w/w}$/tablet |
| Tablet mold release | Polyethylene glycol 3350 | 8.0%$^{w/w}$/tablet |

*activity in final solution; @ 30 Anson units (A.U.)/g = 6.67–25.0 mg per tablet
**Di-Pac is a compressible sugar. It is comprised of 97%$^{w/w}$ sucrose and 3%$^{w/w}$ maltodextrin. Di-pac is available from Amstar Sugar Corporation and is distributed by Austin Chemical Co., Illinois
***polyvinylpyrrolidone Aqueous solution of disinfecting/sterilizing agent*

| Functional Component | Raw Material | Concentration %$^{w/v}$ |
|---|---|---|
| Disinfecting agent | hydrogen peroxide | 0.50–1.50 |
| Disinfecting agent | peracetic acid | 0.05–0.30 |
| H$_2$O$_2$ stabilizer | Dequest 2010 | 0.10–1.0 |

*also contains an amount of acetic acid corresponding to the amount of peracetic acid and hydrogen peroxide in equilibrium The above composition is illustrative for kidney dialyzer applications in that it contains few components other than per-compounds and enzyme, which is preferable to minimize potential patient exposure to chemicals. Alternatively, the enzyme may be contained in a liquid formula, preferably stabilized with a sugar-based polyol such as sorbitol and an appropriate buffer. It is also preferable for dialyzer applications to utilize a 10–35 fold concentrate for the disinfecting/sterilizing solution, which is diluted with suitable purified water just prior to mixing with the enzyme and prior to use.

The following examples are presented to illustrate, but not limit, the scope of this invention. Alcalase® 2.5 L was obtained from Novo Nordisk. Azocasein, a protein substrate for Alcalase®, was obtained from Sigma. Abs$_{390}$= absorbance measured on a spectrophotometer with wavelength set at 390 nm. A.U.=Anson Units. The following examples which incorporate H$_2$O$_2$ alone are not illustrative of the scope of the invention, since H$_2$O$_2$ alone does not achieve high- and intermediate-level decontamination. However, it is necessary to sufficiently stabilize H$_2$O$_2$, since destabilization of H$_2$O$_2$ will cause destabilization of peracids such as PAA or other peracids derived from an equilibrium mixture of H$_2$O$_2$ and a precursor organic acid.

EXAMPLE 1

Sporicidal Activity of Combined Proteolytic Enzyme and Hydrogen Peroxide (H$_2$O$_2$) Solutions The Association of Official Analytical Chemists (AOAC) test for Sporicidal Activity of Disinfectants, AOAC Official Methods of Analysis, 15th edition, 1995, was employed to evaluate the sporicidal activity of combinations of proteolytic enzyme and solutions containing H$_2$O$_2$.

No organic soil load was used for this example. Clean porcelain penicylinders (O.D. 8 mm±1 mm, I.D. 6 mm±1 mm, length 10 mm±1) were sterilized in a 180° C. air oven for 2 h. Carriers were immersed for 15 min in a 72±4 h old broth culture containing spores of *Bacillus subtilis* (ATCC #19659) in soil extract-nutrient medium at a ratio of one carrier/ml broth culture, and carriers were placed into a glass petri dish matted with two layers of filter paper. The contaminated carriers were transferred in a vacuum desiccator containing $CaCl_2$ and the vacuum was drawn to 69 cm (27 inches) Hg for 20 min The contaminated carriers were dried in a desiccator for 42 h.

Test solutions of proteolytic enzyme and $H_2O_2$ were placed into duplicate test tubes and equilibrated to 20° C. in a water bath for 10 min. Five contaminated porcelain penicylinder carriers were placed into each of two tubes containing the individual test solutions. After a defined period of contact representing the sterilization time, the carriers were individually removed by hook needle to a subculture medium of Fluid Thioglycollate Medium USP. After completion of subcultures, each carrier was re-transferred to a fresh tube of the same subculture medium and incubated for 21 days at 37±2° C. After 21 days the tubes were examined for growth as determined by turbidity. Tubes demonstrating growth were subcultured onto agar medium for confirmation of the test organism. Tubes demonstrating no growth of the test organisms were heat shocked for 20 min at 80±1° C. and reincubated for 72±4 h at 35–37° C. Tubes without growth following the heat shock treatment were considered negative.

Two concentrations of $H_2O_2$, 6.5 and 15.0% $^{w/w}$ were utilized for this test. These were prepared from a 35.1 % $^{w/w}$ solution of $H_2O_2$ in water (Aldrich Chemical Company, lot #06004 diluted with the required amount of deionized water. The proteolytic enzyme utilized for this test was subtilisin-A from *B. licheniformis* (Novo Nordisk A/S in Bagsvaerd, Denmark, hereinafter Novo). The subtilisin-A was prepared in 135.4 mg tablets containing 0.4 mg subtilisin raw material representing 0.012 A.U. enzyme activity/ tablet. One tablet was dissolved in 10.0 ml of one of the aforementioned $H_2O_2$ solutions for each test, 16 min prior to exposure of the contaminated penicylinder to the test solution. Thus, the final enzyme concentration in the $H_2O_2$ solutions representing each of the test solutions in Table 1 was 0.0012 A.U./ml. Each enzyme tablet also contained 40 mg sorbitol, 52 mg sodium carbonate, 7 mg tartaric acid, 30 mg N-acetyl cysteine and 6 mg polyethylene glycol 3350 for formulating purposes. The enzyme tablets contained sodium carbonate as an alkaline buffer which increased the pH of the $H_2O_2$ solutions to the final pH indicated in Table 1. The final pH varied with the concentration of $H_2O_2$ since the original concentrated $H_2O_2$ contained acid to maintain a low pH for stability. The final pH values reported in Table 1 are within the known pH activity range of subtilisin-A. Deionized water was used as a negative control.

TABLE 1

| Sample # | $H_2O_2$ % $^{w/w}$ | pH | Enzyme | Exposure | Results |
|---|---|---|---|---|---|
| 1 | D.I. Water | | | 60 min | 10 positive |
| 2 | 6.5 | 8.6 | subtilisin-A | 30 min | 10 positive |
| 3 | 6.5 | 8.6 | subtilisin-A | 45 min | 10 positive |
| 4 | 6.5 | 8.6 | subtilisin-A | 60 min | 10 positive |
| 5 | 6.5 | 8.6 | subtilisin-A | 120 min | 1 positive |
| 6 | 15.0 | 7.8 | subtilisin-A | 15 min | 10 positive |
| 7 | 15.0 | 7.8 | subtilisin-A | 30 min | 10 positive |
| 8 | 15.0 | 7.8 | subtilisin-A | 45 min | 9 positive |
| 10 | 15.0 | 7.8 | subtilisin-A | 60 min | 3 positive |
| 11 | 15.0 | 7.8 | subtilisin-A | 60 min | 2 positive |

The results, shown in Table 1, indicated that while none of the solutions achieved complete sterilization, an increasing exposure time for a given $H_2O_2$ concentration resulted in fewer positive penicylinders. It is also clear that a higher $H_2O_2$ concentration achieves a greater reduction in positive penicylinders in the same exposure time than a lower concentration. The results of Example 1 were utilized to design a second microbiology experiment to test the capacity of a combination $H_2O_2$-containing and subtilisin-A solution to achieve sporicidal activity within the 20-hour time limit imposed by the Food and Drug Administration (FDA) as a sterilization standard for high-level disinfection solutions.

EXAMPLE 2

Sporicidal Activity of Combined Proteolytic Enzyme and Hydrogen Peroxide Solutions The microbiology test method, test solutions and enzyme tablets the same as in Example 1 but the $H_2O_2$ concentrations and exposure times were different. Control $H_2O_2$ solutions without subtilisin-A were adjusted from the original pH 3.9 to either pH 5 with potassium dihydrogenphosphate and dipotassium hydrogen phosphate, or to pH 7 with sodium carbonate and potassium dihydrogenphosphate. The same concentration of subtilisin-A (0.0012 A.U./ml of $H_2O_2$) was utilized for each test solution except the control $H_2O_2$ solutions.

The results are presented in Table 2. Subtilisin-A solutions containing 7.5%, 4.9% and 2.5% $H_2O_2$ were sporicidal (no positive penicylinders) at 3, 8 and 10 h, respectively. Solutions of 7.5% $H_2O_2$ alone at a pH in the range of about 3.9–7 were all sporicidal within 4 h. The inherent sporicidal activity of $H_2O_2$ was not reduced with the addition of subtilisin-A (compare test number 7 with numbers 10–12). The difference in pH is not considered significant here, as it has been reported that sporicidal activity of $H_2O_2$ does not differ between pH 6.5 and 8.0 and increases at pH 5. The bactericidal, fungicidal and sporicidal properties of hydrogen peroxide and peracetic acid (Baldry, M. G. C., *J App Bact*, 1983; 54:417–423). This demonstrates that a combination of a proteolytic enzyme such as subtilisin-A with $H_2O_2$ can achieve sterilization of spores on an object and thus can meet one of the primary standards for a high-level disinfectant or sterilant for medical devices.

TABLE 2

| Sample # | $H_2O_2$ (% $^{w/w}$) | pH | Enzyme | Exposure (hours) | Results |
|---|---|---|---|---|---|
| 1 | 2.5 | 8.5 | subtilisin-A | 5 hours | 3 positive |
| 2 | 2.5 | 8.5 | subtilisin-A | 10 hours | 0 positive |
| 3 | 4.9 | 8.5 | subtilisin-A | 4 hours | 1 positive |
| 4 | 4.9 | 8.5 | subtilisin-A | 8 hours | 0 positive |
| 5 | 7.5 | 8.5 | subtilisin-A | 2 hours | 4 positive |
| 6 | 7.5 | 8.5 | subtilisin-A | 3 hours | 0 positive |
| 7 | 7.5 | 8.5 | subtilisin-A | 4 hours | 0 positive |
| 8 | 7.5 | 8.5 | subtilisin-A | 6 hours | 0 positive |
| 10 | 7.5 | 7 | — | 4 hours | 0 positive |
| 11 | 7.5 | 5 | — | 4 hours | 0 positive |
| 12 | 7.5 | 3.9 | — | 4 hours | 0 positive |

EXAMPLE 3

Effect of pH on Protease Activity in 7.5% $^{w/w}$ $H_2O_2$

Alcalase® 2.5 L, 0.8 grams (Novo Nordisk) was mixed with 1 liter of 7.5% $^{w/w}$ $H_2O_2$ (diluted from 35% $H_2O_2$ Aldrich) solution at room temperature, thus yielding an initial enzyme activity of 0.002 A.U./ml. At each time point, an aliquot of the mixed solution was removed and assayed for enzyme activity using an Azocasein substrate method (Novo Nordisk). The enzyme solution was allowed to hydrolyze azocasein for 30 min at 40° C. Undigested protein was precipitated with trichloroacetic acid and digested protein was quantitated by spectrophotometry. Standards and samples were prepared using Alcalase® 2.5 L with 0.2 M trishydroxymethylaminomethane (Sigma, "Trizma Base") as a diluent. One ml sample or enzyme standard was added to test tubes and equilibrated to 40° C. for approximately one min. At precisely timed intervals, 5 ml substrate solution was added to each tube. The substrate solution consisted of 0.6%$^{w/v}$ Azocasein powder (Sigma), 5%$^{w/v}$ urea solution, 0.2 M tris(hydroxymethyl)aminomethane buffer at pH 8.5, and the final solution was adjusted to pH 8.5 with dilute $H_2SO_4$. After adding substrate, the solutions were mixed using a vortex mixture and returned to the 40° C. water bath for exactly 30 min, after which time 5 ml 10%$^{w/v}$ trichloroacetic acid (Aldrich) was added to each tube. After room temperature incubation for 15–20 min, the solutions were gravity filtered using Whatman #3 filter paper into clean test tubes and the absorbance of each solution was determined at 390 nm ($Abs_{390}$) on a Shimadzu UV-1601 spectrophotometer using a standard blank. A calibration curve was generated using the standard absorbances, and then linear regression was used to determine the sample enzyme concentrations.

Table 3 shows the enzyme activity in the mixture of 0.8 mg/ml Alcalase® 2.5 L and 7.5%$^{w/w}$ $H_2O_2$ solution at room temperature at pH 3.9. There is considerable loss in enzyme activity almost immediately due to the stressed condition of 7.5% $H_2O_2$ (data not shown). At 240 min, however, there is partial recovery of enzyme activity.

After the initial 30 min, the mixed enzyme/$H_2O_2$ solution was split into two parts; one part remained unchanged and 2 M Tris buffer was added to the other part in a volume ratio of 9:1 to achieve 0.2 M Tris at pH 8.5. As shown in Table 3, recovery of enzyme activity was more striking in 0.2 M Tris buffer at pH 8.5 than at pH 3.9. This phenomenon was also observed in a mixed solution of Alcalase®/PAA—$H_2O_2$. It is yet to be determined if the enzyme activity recovery occurred in the enzyme/$H_2O_2$ mixed solutions or during the enzyme activity assay. This example, however, demonstrated the pH effect on enzyme activity in the presence of a high concentration of hydrogen peroxide.

TABLE 3 pH Effect on Alcalase ® activity (AU/ml) in 7.5%$^{w/w}$ $H_2O_2$ solution

| Time (# min) | (3.9 pH unadjusted) | 8.5 (pH adjusted) in 0.2 M Tris buffer |
|---|---|---|
| 3.5 | 0.82 | |
| 30 | | 0.20 |
| 120 | 0.19 | 0.31 |
| 240 | 0.35 | 0.56 |

EXAMPLE 4

Effect of pH on Protease Activity in 7.5%$^{w/v}$ $H_2O_2$ Solutions

The enzyme activity lost under stressed conditions, such as in $H_2O_2$ or PAA solutions at concentrations capable of achieving sporicidal activity ($H_2O_2$) or high-or intermediate-level disinfection and sterilization (PAA), respectively, can be partially recovered after an aliquot of the solution is diluted with 0.2 M Tris buffer (as in the enzyme manufacturer's recommended method for determining enzyme activity). Thus, in this example, an in-situ protease activity assay method was employed which deviated from the manufacturer's method but better mimicked the real cleaning process.

Solutions of 7.5%$^{w/v}$ $H_2O_2$ at various pH levels were prepared by adjusting the pH of 35%$^{w/w}$ $H_2O_2$ solution (Degussa) with 10 mM $K_3PO_4$ in a volumetric flask in the presence of $K_2HPO_4$ (phosphate buffer, PB). The solution was diluted with 10 mM $KH_2PO_4$ solution of the same pH. The 7.5%$^{w/v}$ $H_2O_2$ solutions were then mixed with Alcalase® 2.5 L in a volume ratio of 1280:1 and thus, had an initial enzyme activity of 0.002 A.U./ml. Azocasein powder was added to the $H_2O_2$/Alcalase® mixed solutions to yield 0.4%$^{w/v}$ azocasein. After 30 min at 23° C., 5 ml azocasein solution was mixed with 5 ml 10%$^{w/v}$ TCA solution. Precipitates were removed after 15 min by filtration, and the supernatant $Abs_{390}$ was measured. As a comparison for the cleaning efficacy, 0.4%$^{w/v}$ azocasein was also added to 10 mM potassium phosphate buffer solutions mixed with Alcalase® 2.5 L in the same volume ratio of 1280:1 but without $H_2O_2$. The absorbance of two other azocasein solutions (0.4%$^{w/v}$) containing 7.5%$^{w/v}$ $H_2O_2$/phosphate buffer and phosphate buffer alone, respectively, without Alcalase® 2.5 L were measured as controls. While azocasein dissolves within a few minutes with stirring in all of the above solutions at pH 8 and pH 5, it virtually did not dissolve at pH 2. The results are given in Table 4 as absorbance of hydrolyzed azocasein solution at 390 nm containing 7.5%$^{w/v}$ $H_2O_2$ and Alcalase® 2.5 L at various pH values at 23° C. The volume ratio of $H_2O_2$ solution or 10 mM potassium phosphate buffer to Alcalase® 2.5 L was 1280:1.

TABLE 4 pH effect on Alcalase ® activity (A.U./ml) in 7.5%$^{w/w}$ $H_2O_2$ solution

| | 7.5%$^{w/w}$ $H_2O_2$/ Phosphate Buffer control | 7.5%$^{w/w}$ $H_2O_2$/ Phosphate Buffer/ Alcalase ® 2.5 L | 10 mM Potassium Phosphate Buffer/ Alcalase ® 2.5 L | 10 mM Potassium Phosphate Buffer control |
|---|---|---|---|---|
| pH 8.0 | 0.0662 | 2.909 | 1.783 | 0.0455 |
| pH 5.0 | 0.0624 | 1.895 | 1.023 | 0.0481 |
| pH 2.0 | 0.0536 | 0.0522 | 0.0323 | 0.0287 |

Although the azocasein substrate can be dissolved in the solutions at pH 8 and pH 5, the $Abs_{390}$ of the solutions without enzyme remained as low as that of the solution at pH 2. In contrast, the $Abs_{390}$ with enzyme solutions increased about 40-fold. Table 4 also shows that the azocasein hydrolysis rate had no significant change within 30 min in the presence of enzyme when azocasein was poorly dissolved in the solutions at pH 2. At pH 8 and pH 5 respectively, the azocasein hydrolysis rate was 1.6 and 1.9 times higher in 7.5%$^{w/v}$ $H_2O_2$ solutions containing enzyme than in the corresponding phosphate buffer PB solutions containing enzyme, indicating the existence of synergism in protein hydrolysis/cleaning efficiency between $H_2O_2$ and enzyme.

EXAMPLE 5

Compatibility of Various Protease Enzymes with $H_2O_2$ Solutions Over Time

The initial $H_2O_2$/enzyme mixed solutions were prepared following the procedures described in Example 4. One half hour prior to various time points (listed in Tables 5a–d), azocasein powder was added to the solution in an amount of 0.4% of the total solution weight. $Abs_{390}$ of the solution was measured as in Example 4 except that the supernatant was diluted 6–7 fold to avoid saturation of the UV spectrophotometer. The results are presented in Tables 5a–5d for the protease enzymes Alcalase, Neutrase, chymotrysin and Savinase respectively.

TABLE 5a

Effect of pH and Time on Alcalase ® compatibility with $H_2O_2$ solutions

| pH | Time (hours) | 7.5%$^{w/v}$ $H_2O_2$/ Phosphate Buffer control | 7.5%$^{w/v}$ $H_2O_2$/ Phosphate Buffer/ Alcalase ® | 10 mM Phosphate Buffer/ Alcalase ® | $Abs_{390}$ Ratio of Alcalase/ Azocasein solutions with and without 7.5% w/v $H_2O_2$ |
|---|---|---|---|---|---|
| 8.0 | 0.5 | 0.0662 | 2.909 | 1.783 | 1.63 |
|  | 2.5 | 0.1644 | 5.728 | 3.172 | 1.81 |
|  | 5.5 | 0.2611 | 8.363 | 4.528 | 1.85 |
|  | 8 | 0.389 | 9.843 | 5.491 | 1.79 |
| 5.0 | 0.5 | 0.0624 | 1.895 | 1.023 | 1.85 |
|  | 2.5 | 0.1238 | 3.948 | 2.077 | 1.90 |
|  | 5.5 | 0.2041 | 6.551 | 3.202 | 2.05 |
|  | 8 | 0.3145 | 7.967 | 3.872 | 2.06 |

The results in Table 5a are obtained as follows: (dilution factor)×($Abs_{390}$) hydrolyzed azocasein solution containing 7.5%$^{w/v}$ $H_2O_2$ and Alcalase® 2.5 L at 23° C. at either pH 5.0 or pH 8.0. The mixing volume ratio of 7.5%$^{w/v}$ $H_2O_2$/PB to Alcalase® 2.5 L was 1280:1.

The cumulative enzyme activity with 7.5% $H_2O_2$ solution was not only about 1.6–2.0 higher than that without $H_2O_2$, but was either constant or even slightly increased over the 8 hour period. These results implied that Alcalase® was stable in and compatible with 7.5% $H_2O_2$ solutions for at least 8 h at pH 5–8. This demonstrated the potential reusability of a combination cleaning and high- or intermediate-level disinfecting or sterilizing solution containing high concentrations of hydrogen peroxide in combination with a peracid. Although the absolute enzyme activity at pH 5 was slightly lower than at pH 8, the relative enzyme activity of the solution with $H_2O_2$ to that without $H_2O_2$ was higher at pH 5.

Table 5b shows results from an additional experiment employing the same method but with the enzyme Neutrase® 0.5 L. These results are presented, normalized with the dilution factor as $Abs_{390}$ hydrolyzed azocasein solution containing 7.5%$^{w/v}$ $H_2O_2$ and Neutrase® 0.5 L at pH 5.6 at 23° C. The mixing volume ratio of 7.5%$^{w/v}$ $H_2O_2$/PB to Neutrase® 0.5 L was either 1280:1 or 2560:1, and the nominal enzyme activity was 0.00048 and 0.00024 A.U./ml, respectively.

An additional experiment employing the same method was conducted with human chymotrypsin. The results are presented in Table 5c as $Abs_{390}$ hydrolyzed azocasein solution by human chymotrypsin with and without $H_2O_2$ at 23° C. and at pH 7.75.

TABLE 5c

Effect of Time on Chymotrypsin compatibility with $H_2O_2$ solutions

| Time (h) | 7.5% $H_2O_2$/ 10 mM phosphate buffer control | Chymotrypsin (25.6 µg/mL) in 7.5% $H_2O_2$/10 mM phosphate buffer | Chymotrypsin (25.6 µg/mL in 10 mM phosphate buffer | Absorbance Ratio of Chymotrypsin/ Azocasein solutions with and without 7.5% $H_2O_2$ |
|---|---|---|---|---|
| 2 | 0.2818 | 0.7814 | 2.541 | 0.308 |
| 4 | 0.2599 | 1.156 | 3.653 | 0.316 |

Lower enzyme activity was seen in the presence of the $H_2O_2$ solution than in the phosphate buffer solution alone. However, substantial enzyme activity remained and even increased over time.

TABLE 5d

Absorbance (normalized with dilution factor) of hydrolyzed Azocasein solution at 390 nm containing 7.5%$^{w/v}$ $H_2O_2$, 0.2%$^{w/v}$ Savinase ™ 16.0 L and/or 1%$^{w/v}$ benzotriazole at pH 8.5 at 23° C. All the solutions contained 7.4 mM $Na_3PO_4$, 1%$^{w/v}$ Azocasein and the solution pH was adjusted to 8.5 with HCl or NaOH solutions.

| Time (h) | $H_2O_2$ Benzotriazole | $H_2O_2$ Benzotriazole Savinase ™ 16.0 L | Benzotriazole Savinase ™ 16.0 L | Benzotriazole |
|---|---|---|---|---|
| 0.5 | 0.1539 | 6.803 | 3.677 | 0.0986 |
| 4.5 | 0.3092 | 7.063 | 5.494 | 0.1536 |

These results show that the corrosion inhibitor benzotriazole alone or $H_2O_2$/benzotriazole mixed solutions do not have significant proteolytic activity and that benzotriazole is compatible with the mixed systems of $H_2O_2$/Savinase™ 16.0 L. It is expected from these results that benzotriazole

TABLE 5b

Effect of Time on Neutrase ® compatibility with $H_2O_2$ solutions

| Time (h) | volume ratio (7.5%$^{w/v}$ $H_2O_2$ Neutrase ®) | 7.5%$^{w/v}$ $H_2O_2$/ 10 mM Phosphate Buffer control | 7.5%$^{w/v}$ $H_2O_2$/ 10 mM Phosphate Buffer/ Neutrase ® | Azocasein Phosphate Buffer/ Neutrase ® | Absorbance Ratio of Neutrase ®/ solutions with and without 7.5% w/v $H_2O_2$ |
|---|---|---|---|---|---|
| 2 | 2560:1 | 0.1513 | 3.063 | 2.172 | 1.41 |
| 5 | 2560:1 |  | 4.697 | 3.410 | 1.38 |
| 2 | 1280:1 | 0.1826 | 4.47 | 2.994 | 1.49 |
| 5 | 1280:1 |  | 6.032 | 4.220 | 1.43 |

These results demonstrated the feasibility of utilizing an enzyme with a more neutral or even slightly acidic pH profile.

will also be compatible with mixed enzyme and $H_2O_2$ plus peracid solutions, which would be capable of meeting high- or intermediate-level disinfection requirements.

EXAMPLE 6
Na$_2$EDTA Stabilization of H$_2$O$_2$ in Enzyme/Bovine Hemoglobin Solutions Table 6 shows the H$_2$O$_2$ concentration change over a period of 28 hours in solutions containing H$_2$O$_2$, Na$_2$EDTA, Alcalase® 2.5 L and bovine hemoglobin (Sigma, St. Louis, Mo.). The concentrations, other than that at 28 h, were initial concentrations after mixing 7.5%$^{w/w}$ H$_2$O$_2$ with Na$_2$EDTA powder, 15%$^{w/w}$ bovine hemoglobin, 10.7%$^{w/v}$ Alcalase® 2.5 L formulation (see Table 7c formula D), and NaOH to adjust pH. Initial Alcalase® activity was 0.092–0.094 A.U./ml. The assay was performed at room temperature. H$_2$O$_2$ concentration measurement was based upon a standard method utilizing a KMnO$_4$ titration.

TABLE 6

Effect of Na$_2$EDTA on H$_2$O$_2$ stability in H$_2$O$_2$/enzyme/bovine hemoglobin solutions.

| Samples | 1 | 2 | 3 | 4 | 5 | 6 |
|---|---|---|---|---|---|---|
| H$_2$O$_2$ %w/w at time 0 | 7.08 | 7.08 | 7.08 | 7.08 | 7.08 | 6.93 |
| Na$_2$EDTA %$^{w/v}$ | 0 | 0 | 0 | 0.11 | 0.28 | 2.76 |
| Alcalase ® 2.5 L %$^{w/v}$ | 0 | 3.77 | 3.77 | 3.77 | 3.77 | 3.69 |
| Bovine Hemoglobin %$^{w/w}$ | 0.28 | 0 | 0.28 | 0.28 | 0.28 | 0.28 |
| H$_2$O$_2$ %$^{w/w}$ after 28 h | 5.18 | 6.73 | 2.51 | 6.79 | 5.99 | 5.30 |
| H$_2$O$_2$ reduction | 27% | 5% | 65% | 4% | 15% | 25% |

Hemoglobin significantly reduced H$_2$O$_2$ concentration, with a 13 fold faster reduction with hemoglobin present (solution 3) than with hemoglobin absent (solution 2). However, in the presence of 0.11 %$^{w/v}$ Na$_2$EDTA, H$_2$O$_2$ was as stable with hemoglobin as without hemoglobin (compare solutions 4 and solution 2). With further increases in Na$_2$EDTA concentration, however, the stability of H$_2$O$_2$ decreases (solutions 5 and 6). While the scientific literature indicates that Na$_2$EDTA consistently accelerates Fenton-reactions such as the hemoglobin-mediated degradation of H$_2$O$_2$, these results surprisingly show that a solution of enzyme and H$_2$O$_2$ can be stabilized against a principle component of blood with the proper level of Na$_2$EDTA. This further demonstrates the reusability of simultaneous cleaning and disinfecting solutions of the present invention containing high concentrations of hydrogen peroxide.

EXAMPLE 7
Effect of Chelating and Other Stabilizing Agents on H$_2$O$_2$ Stability in Enzyme/Blood Solutions Fifty ml of 7.5%$^{w/w}$ H$_2$O$_2$ solution, prepared by diluting 35%$^{w/w}$ H$_2$O$_2$ solution (Degussa), was mixed with 1 ml of chelating agent (in solution at various concentrations), 1.95 ml of the enzyme formulation containing 10.7%$^{w/v}$ Alcalase® 2.5 L (see formula D, Table 7c), and 1.1 ml duck blood. Na$_2$EDTA and phenanthroline chelating agents were tested. Na$_2$EDTA solutions were adjusted to pH 8.1 using Tris buffer, and Alcalase® 2.5 L formulations were similarly adjusted to pH 8.5. The pH of phenanthroline solutions was not adjusted. Table 7a lists the concentrations of H$_2$O$_2$, chelating agents, Alcalase® 2.5 L and duck blood, as well as pH values after mixing. For mixed solutions without chelating agent and/or duck blood, 1 ml or 2.1 ml distilled water was added so that the resulting concentrations of H$_2$O$_2$ and Alcalase® 2.5 L were the same. The initial Alcalase® enzyme activity was about 0.0098 A.U./ml. The H$_2$O$_2$ concentrations of the mixed solutions were measured using a standard KMnO$_4$ titration method and traced for 5 days. The results are listed in Table 7a.

TABLE 7a

Effect of chelating agents on H$_2$O$_2$ stability in solutions containing enzyme and duck blood at room temperature.

| Samples | 1 | 2 | 3 | 4 | 5 | 6 |
|---|---|---|---|---|---|---|
| H$_2$O$_2$ %$^{w/w}$ at time 0 | 6.93 | 6.93 | 6.93 | 6.93 | 6.93 | 6.93 |
| Na$_2$EDTA %$^{w/v}$, pH 8.1 | 0.31 | 0.06 | 0 | 0 | 0 | 0 |
| Phenanthroline (mM) | 0 | 0 | 9.26 | 1.85 | 0 | 0 |
| Alcalase ® 2.5 L %$^{w/v*}$ | 0.39 | 0.39 | 0.39 | 0.39 | 0.39 | 0.39 |
| Duck blood %$^{w/v}$ | 2.04 | 2.04 | 2.04 | 2.04 | 2.04 | 0 |
| pH | 8.03 | 8.07 | 7.8 | 6.47 | 8.02 | 8.28 |
| H$_2$O$_2$ %$^{w/w}$ after 1 day | 6.46 | 6.46 | 3.18 | 1.87 | 5.81 | 6.93 |
| H$_2$O$_2$ %$^{w/w}$ after 5 days | 5.43 | 4.68 | 1.78 | 1.78 | 1.97 | 6.84 |

*An enzyme formulation containing 10.7% Alcalase ® 2.5 L in 1 M Tris buffer at pH 8.5 was used (see formula D, Table 7c).

H$_2$O$_2$ was very unstable in the absence of chelating agents (solution 5), losing 16% and 72% over 1 and 5 days, respectively. Addition of phenanthroline at pH 7.8 and 6.47 (solutions 3 and 4) causes H$_2$O$_2$ to be even more unstable. In the presence of Na$_2$EDTA, however, H$_2$O$_2$ stability was significantly enhanced, losing only 7% and 22–32% for 1 and 5 days, respectively (solutions 1 and 2). These results demonstrated that a solution of enzyme and H$_2$O$_2$ can be stabilized to retain activity even in the presence of blood with the proper concentration of Na$_2$EDTA, and further demonstrate the reusability of simultaneous cleaning and disinfecting solutions of the present invention containing high concentrations of hydrogen peroxide.

Table 7b shows the results of using H$_2$O$_2$ stability seven days after 100 ml 7.5%$^{w/v}$ H$_2$O$_2$ solution was mixed with 0.775 ml enzyme formulation and various amount of organic soils (duck blood or calf serum) at 23° C. The pH of the mixed solution was 8.0±0.1.

TABLE 7b

| Enzyme Formulation (see Table 7c) | 7.5% H$_2$O$_2$$^{w/v}$ (ml) | Duck Blood (ml) | H$_2$O$_2$ %$^{w/v}$ by titration |
|---|---|---|---|
| 0.775 ml E | 100 | 0.16* | 7.50 |
| 0.775 ml F | 100 | 0.16 | 6.87 |
| 0.775 ml G | 100 | 0.16 | 7.27 |
| 0.775 ml H | 100 | 0.16 | 7.33 |

*calf serum

TABLE 7c

| Formulation | A %$^{w/v}$ | B %$^{w/v}$ | C %$^{w/v}$ | D %$^{w/v}$ | E %$^{w/v}$ | F %$^{w/v}$ | G %$^{w/v}$ | H %$^{w/v}$ |
|---|---|---|---|---|---|---|---|---|
| Alcalase ® 2.5 L | 10.7 | 10.5 | 10.4 | 10.7 | 10.7 | 10.7 | 10.7 | 10.7 |
| Dowicide 1 | 0.10 | 0.09 | 0.09 | 0.10 | 0.10 | 0.1 | 0.1 | 0.1 |
| Makon 10 | 15.2 | 14.9 | 14.7 | 15.0 | 15.0 | 7.0 | 7.0 | 7.0 |
| Deionized water | 33.7 | 34.0 | 34.4 | 37.5 | 41.7 | 40.3 | 40.3 | 40.3 |
| Peppermint oil | 0.02 | 0.02 | 0.02 | | | 0.02 | 0.02 | 0.02 |

TABLE 7c-continued

| Formulation | A %w/v | B %w/v | C %w/v | D %w/v | E %w/v | F %w/v | G %w/v | H %w/v |
|---|---|---|---|---|---|---|---|---|
| FD&C blue dye #1 | 0.00 | 0.004 | 0.004 | 0.01 | 0.01 | 0.004 | 0.004 | 0.004 |
| Antifoam C | 0.03 | 0.03 | 0.03 | 0.03 | 0.03 | 0.05 | 0.05 | 0.05 |
| Propylene Glycol | 23.0 | 22.5 | 22.3 | 23.0 | 23.0 | 33.4 | 33.4 | 33.4 |
| Tris | | | | 12.1 | 8.4 | 8.4 | 8.4 | 8.4 |
| $H_2SO_4$ | 0.12 | 1.20 | | | | | | |
| Acetic acid | | | 1.46 | 1.50 | 1.05 | | | |
| TEA 85% | 17.2 | 16.8 | 16.6 | | | | | |
| $H_3BO_3$ | | | | | | | 0.024 | 0.048 |

These results demonstrated that enzyme formulations with various buffer systems can maintain $H_2O_2$ concentrations.

Another example, which follows, illustrates the utility of a boric acid ($H_3BO3$) buffer in the compositions of the present invention.

TABLE 7d $H_2O_2$ stability in enzyme/blood systems with borate salt as a stabilizer (3.7%$^{w/w}$ formula G in Table 7c used for all examples, which contributes 0.14 mM $H_3BO_3$.

| | Sample 1 | Sample 2 | Sample 3 | Sample 4 |
|---|---|---|---|---|
| $H_2O_2$ % initial | 7.14 | 7.14 | 7.14 | 7.22 |
| $H_3BO_3$ added | 40. mM | 8. mM | 0 | 0 |
| Enzyme Alcalase 2.5L %w/v | 0.40 | 0.40 | 0.40 | 0.40 |
| Duck Blood % | 1.10 | 1.10 | 1.10 | 0 |
| $H_2O_2$ after 3 days % | 7.02 | 6.28 | 5.84 | 7.22 |
| Second addition of $H_3BO_3$ | Yes | Yes | No | No |
| Total $H_3BO_3$ mM | 80.1 | 16.1 | 0.14 | 0.14 |
| Total Duck Blood % | 2.20 | 2.20 | 2.20 | 0 |
| $H_2O_2$ % after 5 days | 5.98 | 2.43 | 2.15 | 6.81 |

It can be seen that in the presence of duck blood, only sample 1 containing 80 mM boric acid maintained hydrogen peroxide concentration at 6%.

The following examples illustrate the effect of boric acid on hydrogen peroxide stability in a combined enzyme-peroxide formulation in the presence of an anticipated amount of whole blood which would be expected to be present under real use conditions in a solution system designed for reprocessing multiple endoscopes over an 8 day period.

TABLE 7e $H_2O_2$ Stability in $H_2O_2$-$H_3BO_3$-Enzyme-Blood Systems
Part A: 2 gallons 7.5% $H_2O_2$, Part B: 2 ounces enzyme formulation (Table 7c- formula F, added at day 0, 3, 4, 5 and 6), Part C: simulation of 0.5 ml duck blood per endoscope and 32 endoscopes per day: 16 ml of blood added at each day.

| Solution | Part C | day 0 | day 3 | day 4 | day 5 | day 6 |
|---|---|---|---|---|---|---|
| 95A | None | | | 7.64 | 7.24 | 7.14 |
| LC17795B | 0.5 ml duck blood | 7.64 | 7.54 | 7.42 | | 5.76 |
| LC17795C | 0.5 ml duck blood/ 40 mM $H_3BO_3$ Part B | | 7.60 | 7.64 | 6.91 | 5.66 |
| LC17795D | 0.25 ml duck blood instead of 0.5 ml | | 7.74 | 7.54 | 7.38 | 6.89 |
| LC17795E | 0.5 ml calf serum instead of 0.5 ml blood | | 7.62 | 7.59 | 7.74 | 7.49 |
| LC17795F | 0.5 ml blood + 0 mM $H_3BO_3$ in final solution | 7.64 | 7.55 | 7.68 | 7.09 | 6.60 |

TABLE 7e-continued $H_2O_2$ Stability in $H_2O_2$-$H_3BO_3$-Enzyme-Blood Systems
Part A: 2 gallons 7.5% $H_2O_2$, Part B: 2 ounces enzyme formulation (Table 7c- formula F, added at day 0, 3, 4, 5 and 6), Part C: simulation of 0.5 ml duck blood per endoscope and 32 endoscopes per day: 16 ml of blood added at each day.

| Solution | Part C | day 0 | day 3 | day 4 | day 5 | day 6 |
|---|---|---|---|---|---|---|
| ZJY17833B | 0.5 ml blood + 0.8 mM $H_3BO_3$ in final solution | | 7.60 | 7.67 | 7.50 | 7.27 |
| ZJY17833C | 0.5 ml blood + 1.6 mM $H_3BO_3$ in final solution | | 7.61 | 7.73 | 7.56 | 7.45 |

TABLE 7f $H_2O_2$ Concentration versus Time. 1 ounce enzyme formulation (pH 8.8) and 16 ml duck blood were added to 1 gallon of 7.5% $H_2O_2$ solutions on cumulative day 0, 1, 2, 3, 6
50 ml $H_2O_2$ 7.5%

| Time (d) | Time (h) | 24F (ml) | pH | Blood (g) | $H_2O_2$ Concentration |
|---|---|---|---|---|---|
| | 0 | 0.387 | | 0.16 | 7.5 |
| | 23 | | 7.9 | | |
| 1 | 24 | 0.387 | | 0.16 | |
| | 47 | | 7.96 | | |
| 2 | 48 | 0.387 | | 0.21 | |
| | 71 | | 7.94 | | |
| 3 | 72 | 0.387 | | 0.21 | |
| | 80 | | 7.87 | | 6.69 |
| | 143 | | 7.12 | | 3.67 |
| 6 | 144 | 0.387 | 7.65 | 0.20 | |
| | 168 | | 6.99 | | 3.11 |
| 7 | 200 | | | | 3.09 |
| | 224 | | | | 2.96 |

The preceding examples of $H_2O_2$ stabilization in the presence of varying amounts of blood indicate that amounts of boric acid between about 1 and 80–100 mM, or 0.006 and 0.62%$^{w/v}$ in the final solution can prevent degradation of $H_2O_2$ over eight days. The results of examples 6 and 7 also indicate that amounts of $Na_2EDTA$ between about 0.05–0.35%$^{w/v}$ in the final solution can prevent degradation of $H_2O_2$.

EXAMPLE 8

Proteolytic Enzyme Cleaning Efficacy in Peracetic Acid (PAA) Solutions at Various pH Solutions of 1.08%$^{w/v}$ $H_2O_2$/0.2 PAA were prepared by diluting a stock of 4.9%$^{w/w}$ PAA (Degussa, density 1.12 g/ml) and pH values were adjusted with 1 N NaOH in the presence of 10 mM $K_2HPO_4$ solution. The PAA/$H_2O_2$ solutions were then mixed with Alcalase® 2.5 L in a volume ratio of 1280:1, yielding a solution with a nominal enzyme activity of 0.0021 A.U./ml. Azocasein powder was added to the $H_2O_2$/Alcalase® mixed solutions to yield an Azocasein concentration of 0.4%$^{w/v}$. After 30 min incubation at 23° C., 5 ml of the Azocasein solution was mixed with 5 ml of 10% TCA solution. After 15 min, the precipitates were filtered, and the supernatant absorbance was measured at 390 nm using a UV-visible spectrophotometer. As a comparison for the cleaning efficacy, Azocasein 0.4%$^{w/v}$ was also added to 10 mM potassium phosphate buffer solutions mixed with Alcalase® 2.5 L in the same volume ratio of 1280:1 but without PAA/$H_2O_2$. The absorbance of two other Azocasein solutions (0.4%$^{w/w}$) containing 0.2% PAA/1.08% $H_2O_2$/phosphate buffer and phosphate buffer alone, respectively, without Alcalase® 2.5 L were measured as a control. While it can be dissolved in all the above solutions at pH 8 and 5 within a few minutes with stirring, Azocasein virtually does not dissolve at pH 2.

The results show the $Abs_{390}$ of hydrolyzed Azocasein solution containing 1.08$^{w/v}$% $H_2O_2$, 0.2$^{w/v}$% PAA and Alcalase® 2.5 L at various pH values at 23° C. The volume ratio of $H_2O_2$/PAA solution or 10 mM potassium phosphate buffer to Alcalase® 2.5 L is 1280:1.

TABLE 8

Effect of pH on Proteolytic Enzyme Cleaning Efficacy in PAA solutions.

| pH | 1.08%$^{w/v}$ $H_2O_2$/0.2%$^{w/v}$ PAA | 1.08%$^{w/v}$ $H_2O_2$/0.2%$^{w/v}$ PAA/ Alcalase ® 2.5 L | 10 mM Potassium Phosphate Buffer /Alcalase ® 2.5 L | 10 mM Potassium Phosphate Buffer |
|---|---|---|---|---|
| 8.0 | 0.2566 | 2.135 | 1.783 | 0.0502 |
| 5.0 | 0.3181 | 1.122 | 1.023 | 0.0459 |
| 2.0 | 0.1284 | 0.1244 | 0.0323 | 0.03 |

Comparing absorbance data in Tables 4 and 8 demonstrate that the mixed solutions of 0.2% PAA/1.08% $H_2O_2$ without enzyme can hydrolyze 4–5 times more Azocasein than a solution of 7.5%$^{w/v}$ $H_2O_2$ without enzyme in the same time period at pH 5 and pH 8. Furthermore, although 0.4% Azocasein was poorly dissolved in the PAA/$H_2O_2$ solutions at pH 2, the partially dissolved Azocasein molecules are hydrolyzed about two times faster than in the 7.5% $H_2O_2$ solutions, with or without enzyme. Table 8 shows that the absorbance of hydrolyzed Azocasein solutions in the mixed solutions of PAA/$H_2O_2$ and enzyme is higher than in the corresponding phosphate buffer solutions containing enzyme at pH 5 and pH 8. The data indicate that synergism in cleaning efficacy exists between PAA/$H_2O_2$ and protease at pH 8, but not at pH 5.

EXAMPLE 9

Proteolytic Enzyme Compatibility with Peracetic Acid Solutions

A solution of 0.2%$^{w/v}$ PAA/1.08%$^{w/v}$ $H_2O_2$ was adjusted to pH 5.6 with 1 N NaOH prior to mixing with Neutrase™ 0.5 L in a volume ratio of 1280:1. The mixed Neutrase™/0.2% PAA/1.08% $H_2O_2$ solution, with a nominal enzyme activity of 0.00048 A.U./ml was then mixed with Azocasein powder to result in 2%$^{w/w}$ Azocasein at 23° C. Three ml of the above solution were removed at each time point and mixed with 3 ml of 10% TCA solution. The precipitates were filtered after 15 min, and the supernatant absorbance was measured at 390 nm using a UV-visible spectrophotometer. As a comparison for the cleaning efficacy, 2 %$^{w/w}$ Azocasein was also added to 10 mM potassium phosphate buffer solutions mixed with Neutrase™ in the same volume ratio of 1280:1 but without PAA/$H_2O_2$, and also at pH 5.6. The absorbance of 2%$^{w/w}$ Azocasein solutions containing 0.2% PAA/1.08% $H_2O_2$/10 mM phosphate buffer, pH 5.6, without Neutrase™ 0.5 L was measured as a control.

Azocasein/TCA solutions were diluted 6–7 fold to avoid saturation of the UV spectrophotometer. The results show absorbance of hydrolyzed Azocasein solution at 390 nm containing 1.08%$^{w/v}$ $H_2O_2$/2.0% PAA and Neutrase™ 0.5 L at pH 5.6 at 23° C.

TABLE 9

| Time (h) | 0.2% PAA/1.08% $H_2O_2$/10 mM $KH_2PO_4$ | 0.2% PAA/1.08% $H_2O_2$/10 mM $KH_2PO_4$ mM Neutrase ™ | 10 mM Potassium Phosphate Buffer /Neutrase ™ |
|---|---|---|---|
| 0.5 | 0.937 | 0.930 | 1.74 |
| 3.0 | 1.46 | 1.37 | 4.00 |

It can be seen that Neutrase™ 0.5 L was 100% inactivated in the solution containing 0.2% PAA and 1.08% $H_2O_2$. Neutrase™ 0.5 L maintained its activity in the presence of 7.5%$^{w/v}$ $H_2O_2$ in example 5b, indicating that enzyme activity in the solutions of the present invention is difficult to predict.

EXAMPLE 10

Enzyme Activity in 0.368%$^{w/v}$ PAA/2%$^{w/v}$ $H_2O_2$, Assayed with Novo Method In a 100 ml volumetric flask, a solution was prepared using 7.5 ml of 4.9%$^{w/w}$ (Degussa) PAA, 1 ml enzyme, and diluted with 0.2 M tris(hydroxymethyl)aminomethane to control the pH at 8.5 to yield a final concentration of 0.368%$^{w/v}$ PAA/2%$^{w/v}$ $H_2O_2$. Two of these solutions were prepared using two different enzymes resulting in a 1%$^{v/v}$ dilution of both Alcalase® 2.5 L and Savinase® 16.0 L. The nominal initial enzyme activity of Alcalase® was 0.0264 A.U./ml in this example. The nominal initial enzyme activity of Savinase® was 0.0529 A.U./ml. The Novo Nordisk assay method described previously was used with a slight modification. A timer was started as soon as the combinations of enzymes and PAA/$H_2O_2$ were mixed. At periodic intervals, aliquots of the enzyme/PAA/$H_2O_2$ solutions were removed and diluted 64 times to react with the 0.6%$^{w/v}$ Azocasein substrate solution in a water bath at the modified temperature of 30° C. for 30 min. After stopping the reaction with 10% TCA and filtering the precipitate, the supernatants were analyzed on a spectrophotometer at 390 nm.

TABLE 10

1%$^{v/v}$ Alcalase ® and 1%$^{v/v}$ Savinase ® proteolytic absorbances in 0.368% PAA/2% $H_2O_2$ solutions.

| | Absorbance | |
|---|---|---|
| Time (h) | 1% Alcalase ® 2.5 L | 1% Savinase ® 16.0 L |
| 0 | 0.6534 | 0.7438 |
| 2.5 | | 0.5611 |
| 3.2 | 0.6417 | |
| 6.5 | 0.6729 | |
| 6.8 | | 0.3973 |
| 7.5 | 0.5689 | |

A 1% solution of Alcalase® had greater stability and proteolytic activity than the 1% Savinase® solution in the presence of 0.368% PAA/2% $H_2O_2$ combination after 6.8 hours. Alcalase® showed a 13% decrease in activity after 7.5 hours and Savinase® showed a 47% decrease after 6.8 hours. These results indicate that Alcalase® is a better candidate than Savinase® for enzyme solutions involving a longer term exposure to high- or intermediate-level disinfecting concentrations of PAA and $H_2O_2$. These data also indicate that the stability of an enzyme in such solutions cannot be predicted a priori, since both enzymes are closely related alkaline serine proteases.

EXAMPLE 11
PAA Stability in Proteolytic Enzyme Solution with Organic Load

Two ml of an enzyme solution containing 10.7% Alcalase® 2.5 L at pH 8.5 (formula D, Table 7c, with additional boric acid ($0.018^{w/v}\%$)) was mixed to a final volume of 50 ml with a solution of $0.2^{w/v}\%$ PAA/$1.0^{w/v}\%$ $H_2O_2$ at 23° C. The resulting solution was pH 8.0 and had a nominal enzyme activity of 0.0107 A.U./ml. Twenty-four hours after bovine hemoglobin powder was added to the above solution, the PAA content was measured using a redox titration method as follows: The sample was weighed (10–15 grams) and transferred to a 250 ml erlenmeyer flask containing 50 ml of 1 N ice-cooled sulfuric acid. After adding two drops of ferroin indicator (Sigma), the $H_2O_2$ content in the sample was reacted with 0.1 N ceric sulfate (Fisher) in a redox titration until the disappearance of a salmon color and the appearance of a light blue color. Ten ml of 2.5 N potassium iodide was added in excess so that the hydroiodic acid formed in the acidic environment would react with PAA to liberate iodine. A standard solution of 0.0206 N sodium thiosulfate was used to titrate the liberated iodine. A few ml of starch indicator were added just after the solution turned brown-yellow, and then additional sodium thiosulfate was added until the solution maintained a salmon color for 15 seconds. The endpoint of the titration was used to calculate the PAA content. Samples without Alcalase or without hemoglobin were also prepared and the PAA content was assayed for comparison.

TABLE 11

PAA Stability in proteolytic enzyme solution with organic load at pH 8 at 23° C.

|  | Sample 1 | Sample 2 | Sample 3 |
|---|---|---|---|
| Alcalase ® 2.5 L (mg/ml) | 0 | 4.28 | 4.28 |
| Hemoglobin (mg/ml) | 2.94 | 0 | 2.94 |
| PAA % at Time 0 | 0.192 | 0.192 | 0.192 |
| PAA % after 24 h | 0.099 | 0.057 | 0.052 |

Table 11 shows that both Alcalase® and bovine hemoglobin cause a decrease in PAA concentration. The mechanism of action of Alcalase and hemoglobin in reducing PAA concentration may be entirely through the reduction of $H_2O_2$ concentration in the solution, which in turn shifts the equilibrium between $H_2O_2$ and PAA toward $H_2O_2$. Alternatively, since the original PAA/$H_2O_2$ solution used herein was a dilution of a more concentrated solution of PAA and was used immediately following dilution, the equilibrium between PAA and $H_2O_2$ may have taken time to re-establish, resulting in the appearance of a loss of concentration of PAA. Nonetheless, the PAA concentration after 24 hours in this system was still above 0.052%, which is above the minimum effective concentration of 0.05% for PAA for a reasonable high- or intermediate-level disinfection time of 25 min at 20° C.

EXAMPLE 12
Peracetic Acid and $H_2O_2$ Disinfecting and Sterilizing Efficacy in Enzyme/blood Systems Sporicidal activity was tested using the method of Example 1 except that 17 days of culture was employed instead of 21 days. Various solutions containing $H_2O_2$ or a mixture of $H_2O_2$ and PAA, with or without $Na_2EDTA$, with or without an Alcalase® 2.5 L enzyme formula and with or without added whole sheep blood were tested. Except where indicated, whole sheep blood was added to the solution just prior to the start of the microbiology experiment. Exposure time was varied according to the concentration of sterilant. Table 12a presents the results.

TABLE 12a

| Peroxide solution (w/v %) | Volume ratio of formulation A/peroxide solution | Volume ratio of sheep blood/peroxide solution | Exposure time/ results at 17 days culture |
|---|---|---|---|
| 7.5% $H_2O_2$ | 0.04 | 0 | 6 hours 0 positive |
| 7.5% $H_2O_2$ | 0.04 | 0.02 | 6 hours 0 positive |
| 7.5% $H_2O_2$ | 0.04 | 0.02* | 6 hours 8 positive |
| 7.5% $H_2O_2$/1 mg/ml $Na_2EDTA$ | 0.04 | 0.02* | 6 hours 0 positive |
| 7.5% $H_2O_2$/2 mg/ml $Na_2EDTA$ | 0.04 | 0.02* | 6 hours 0 positive |
| 0.2% PAA/1% $H_2O_2$ | 0.04 | 0.00 | 8 hours 0 positive |
| 0.2% PAA/1% $H_2O_2$ | 0.04 | 0.02 | 8 hours 0 positive |
| 0.2% PAA/1% $H_2O_2$ | 0.04 | 0.02* | 8 hours 0 positive |
| 0.2% PAA/7.5% $H_2O_2$ | 0.00 | 0.02 | 2 hours 0 positive |
| 0.2% PAA/7.5% $H_2O_2$ | 0.04 | 0 | 30 min; 0 positive 2 hours |
| 0.2% PAA/7.5% $H_2O_2$ | 0.04 | 0.02 | 30 min; 0 positive 2 hours |
| 0.2% PAA/7.5% $H_2O_2$ | 0.04 | 0.02* | 2 hours 0 positive |
| 0.08% PAA | 0.00 | 0.02 | 8 hours 0 positive |
| Peract-20 ™ | 0.04 | 0.02 | 8 hours 0 positive |
| Sporox ® | 0.04 | 0.02 | 6 hours 0 positive |

*Sheep blood was added to the solutions 5 days before the sporicidal microbiology test.

TABLE 12b

| Formulation A | |
|---|---|
| Ingredients | %w/v |
| Deionized Water | 36.7 |
| Tris(hydroxymethyl)aminomethane | 8.82 |
| Acetic Acid | 1.09 |
| Propylene Glycol (enzyme stabilizer) | 34.8 |
| Dowicide 1 (preservative) | 0.101 |
| Antifoam C | 0.0521 |
| Peppermint Oil (fragrance) | 0.0188 |
| FD&C Blue Dye #1 | 0.0041 |
| Makon 10 (surfactant) | 7.29 |
| Alcalase ® 2.5 L | 10.7 |

The results show that a solution containing 7.5% $H_2O_2$, Alcalase® and $2\%^{v/v}$ whole blood can achieve sterilization against *B. subtilis* in 6 h. The results also demonstrate that when whole blood is added to the solution five days prior to the start of the test, the $H_2O_2$ solution is sufficiently destabilized such that sterilization is not achieved. This is believed to be caused by the Fenton-reaction mediated degradation of $H_2O_2$ by hemoglobin. However, with addition of $Na_2EDTA$ to the $H_2O_2$ solution, sterilization is achieved. This result was unexpected, as it has been reported in the literature that $Na_2EDTA$ accelerates the Fenton-reaction. The results additionally demonstrate that solutions containing 0.2% PAA with $H_2O_2$ between 1 and 7.5%, Alcalase® and $2\%^{v/v}$ whole blood can achieve sterilization in various times. The results further demonstrate that a solution containing PAA alone, with Alcalase® and whole blood can achieve sterilization. The results still further demonstrate that existing high- or intermediate-level disinfection and sterilization products such as Peract-20™ and Sporox® can still achieve sterilization in the presence of whole blood when combined with an enzyme formula of the present invention.

The results of examples 10, 11 and 12 indicate that the compositions and methods of the present invention can achieve simultaneous cleaning (e.g., protein removal, etc.) and high-level disinfection or sterilization.

EXAMPLE 13
Enzyme Activity of Human Enzyme/phosphate Buffer/PAA/ hydrogen Peroxide ($H_2O_2$) Mixed Systems with Azocasein as an Organic Soil Model Table 13a lists the enzyme activity data of human trypsin (Sigma) in 10 mM phosphate buffer and in 0.2% PAA/1.05% $H_2O_2$ solution at 23° C. at pH 7.5. The activity for the PAA/$H_2O_2$ solution alone as a control is also given. The initial trypsin/phosphate buffer solution was prepared as follows: 124 µg human trypsin was dissolved in ml of 10 mM $K_3PO_4$ at pH 7.5. A volume of 4.05 ml of 10 mM $K_3PO_4$ buffer was combined with 0.45 ml initial trypsin buffer solution and 45 mg Azocasein to prepare the trypsin/phosphate buffer solution for the test.

A 0.22%$^{w/v}$ PAA/1.17%$^{w/v}$ $H_2O_2$ solution was prepared using a dilution of Degussa's 4.9%$^{w/w}$ PAA/26.6%$^{w/w}$ $H_2O_2$ in a volumetric flask. A volume of 4.05 ml of the latter solution was mixed with 0.45 ml initial trypsin/phosphate buffer solution and 45 mg Azocasein powder. The final concentrations were 12.4 mg/mL trypsin, 0.2%$^{w/v}$ PAA, 1.05%$^{w/v}$ $H_2O_2$ and 1%$^{w/v}$ Azocasein.

As a comparison, the solution to test the activity of PAA/$H_2O_2$ alone on the Azocasein substrate was prepared in the same manner as the solution above, without added trypsin, using a dilution of Degussa's 4.9%$^{w/w}$ PAA/26.6%$^{w/w}$ $H_2O_2$ in a volumetric flask for a concentration of 0.20% PAA/1.05% $H_2O_2$. Azocasein powder was added to the 0.2% PAA/1.05% $H_2O_2$ solution which resulted in a 1%$^{w/v}$ Azocasein protein.

At 2.8 and 7 h, 1.5 ml sample aliquots were removed from the above three solutions and reacted with 1.5 ml of 10%$^{w/v}$ trichloroacetic acid stop reagent. After incubating for 15–20 min, the solutions were filtered using Whatman #3 filter paper with a syringe and a Gelman 13 mm filter holder. The filtered solutions were then analyzed with a Shimadzu UV-visible 1601 spectrophotometer $Abs_{390}$.

TABLE 13a

Absorbance data at 390 nm of hydrolyzed Azocasein solution by the mixed systems of human trypsin/phosphate buffer/PAA/$H_2O_2$ at 23° C. at pH 7.5.

| Time (h) | 0.2% PAA /1.05% $H_2O_2$ /phosphate buffer | Trypsin (1.24 µg/ml) in 10 mM phosphate buffer | Trypsin (1.24 µg/ml) in 0.2% PAA/1.05% $H_2O_2$ /phosphate buffer | Absorbance Ratio of Trypsin/ Trypsin-0.2% PAA/1.05% $H_2O_2$ solutions |
|---|---|---|---|---|
| 2.8 | 0.7581 | 1.4254 | 1.2212 | 0.86 |
| 7 | 0.7152 | 1.5588 | 1.1967 | 0.77 |

The results demonstrate that trypsin is active in the PAA/$H_2O_2$ solution. The data further indicate that there is not a large difference in the proteolytic activity between trypsin alone and trypsin in 0.2% PAA/1.05% $H_2O_2$ solution. An additional example with human chymotrypsin follows. The solutions were similarly prepared as above.

TABLE 13b

Absorbance data at 390 nm of hydrolyzed Azocasein solution by the mixed systems of human chymotrypsin/PAA/$H_2O_2$ at 23° C. at pH 7.25

| Time (h) | 0.1% PAA /0.54% $H_2O_2$/ phosphate buffer | Chymotrypsin (25.6 µg/ml) in 10 mM phosphate buffer | Chymotrypsin (25.6 µg/ml) in 0.1% PAA/0.54% $H_2O_2$/ 10 mM phosphate buffer |
|---|---|---|---|
| 2 | 0.7452 | 2.716 | 1.228 |
| 4 | 0.8320 | 3.674 | 1.262 |

The results show that human chymotrypsin retains significant activity in a PAA/$H_2O_2$ solution suitable for high- or intermediate-level disinfection or sterilization in a reasonable regimen time. Moreover, since it has been previously demonstrated herein that the presence of a proteolytic enzyme such as trypsin or chymotrypsin will not interfere with sterilization and high- or intermediate-level disinfection of an oxidant-based solution such as PAA, the results of Examples 13a and 13b demonstrate that the compositions and methods of the present invention can achieve the requirements for a simultaneous protein removal (cleaning) and high- or intermediate-level disinfection or sterilization system for endoscope or kidney dialyzer reprocessing.

EXAMPLE 14
pH Adjustment of $H_2O_2$ and/or PAA Solutions by Adding Enzyme Formulations To effectively increase the pH of an acidic disinfectant solution, such as a solution containing a large amount of concentrated $H_2O_2$ (e.g., 7.5%$^{w/w}$) in combination with a low concentration of peracid (e.g., 0.2%$^{w/w}$) or a $H_2O_2$/PAA solution, to within a range of 5–9 when mixed with an enzyme formulation, a large amount of buffering agent(s) must be incorporated in the enzyme formulation. This is not only due to the low pH values of acidic $H_2O_2$ and/or PAA solutions at which they are stable, but also because large mixing ratios of $H_2O_2$ and/or PAA solutions to enzyme formulation (i.e., 1 gallon $H_2O_2$-containing solution:1 oz liquid enzyme formulation are required in many practical applications for the compositions and methods of the present invention, especially those applications involving endoscope reprocessing. However, many buffering agents are either insoluble or unstable at the required high concentrations in liquid enzyme formulations which contain a large amount of organic solvents such as propylene glycol to stabilize the enzyme to achieve a reasonable shelf life. For example, prior art buffers such as 0.5–1 M phosphate buffer and borate buffer solutions in the presence of 23% propylene glycol, 15% Makon 10 and 10.7% Alcalase® form two liquid phases and a precipitate, respectively. It was discovered that large amounts of buffering agents can be dissolved in low water content enzyme solutions if proper hydrophobicity of the buffering agent molecules is carefully selected. A tromethamine or Tris buffer, 2-amino-2-hydroxymethyl-1,3-propanediol, paired with an organic acid such as acetic acid, and 2-amino-2-methyl-1-propanol, mono-, di- and triethanolamine (TEA) paired with either an inorganic or organic acid are some of the qualified buffering agents. High Tris buffer concentration sometimes can cause the solution to be metastable if the pH of the mixed enzyme solutions is adjusted with inorganic acid, thus the Tris buffer compositions of the '555 patent are unsuitable. Examples of suitable buffers are presented in Table 14a.

TABLE 14a pH value of the mixed solutions of 7.5%$^{w/w}$ $H_2O_2$ (pH 3.9) and the buffered enzyme formulation. The containers containing the solutions were opened to the air during the test.

| Enzyme formulations (Table 7c) | Molar ratio of acid to buffering agent in the enzyme formulation | pH of the enzyme formulation before mixing with 7.5%$^{w/w}$ $H_2O_2$ | Volume ratio of 7.5% $H_2O_2$ solution to enzyme formulations | |
|---|---|---|---|---|
| | | | 1 gal:1 oz pH of mixed solution | 2 gal:1 oz pH of mixed solution |
| A | $H_2SO_4$:TEA = 0.025 | 9.9 | 8.0 (0 time) | 7.8 (0 time) |
| | | | 7.2 (after 15 h) | 6.7 (after 15 h) |
| B | $H_2SO_4$:TEA = 0.25 | 8.8 | 7.9 (0 time) | 7.7 (0 time) |
| | | | | 7.3 (after 1 h) |
| | | | 6.2 (after 15 h) | 6.1 (after 15 h) |
| C | Acetic acid:TEA = 0.25 | 8.5 | 7.9 (0 time) | 7.6 (0 time) |
| | | | | 7.0 (after 2 h) |
| | | | 6.1 (after 15 h) | 6.0 (after 15 h) |
| D | Acetic acid:Tris = 0.25 | 8.8 | 7.9 (0 time) | |
| | | | 7.8 (after 3 h) | |

Alcalase®, the enzyme utilized in these examples, exerts maximum protein removal efficacy in combination with $H_2O_2$ at a pH greater than about 7 to 7.5. The results of these examples show that all of the buffers evaluated will produce an acceptable initial pH for Alcalase® activity. It is generally desired for solution reuse purposes to have a solution which can be used for at least 1–5 days, especially for endoscope and other semicritical medical device reprocessing. These results show that buffers in accordance with the present invention can achieve the desired pH stability over a one day use period, which is for practical purposes 16 hours (two 8-hour work shifts in a hospital or clinic). It is also clear from the foregoing examples that these buffers could maintain a proper pH for a neutral protease such as Neutrase™ (pH optimum 5.5–7) for an even longer period, provided they were adjusted to a somewhat lower initial pH. The effect of various buffers on enzyme activity over typical solution reuse times as well as short term shelf stability times was evaluated in the examples in Table 14b.

TABLE 14b

Enzyme stability at 40° C. Enzyme formulations are presented in Table 14c.
The Novo azocasein substrate based assay method was utilized to determine enzyme activity presented in Table 14b below.

| Formula | 0 time | 13 days | % change | 28 days | % change |
|---|---|---|---|---|---|
| A | 1.030 | 0.884 | −14 | 0.851 | −17 |
| B | 1.136 | 0.860 | −24 | 0.611 | −46 |
| C | 1.155 | 0.758 | −34 | 0.557 | −52 |
| D | 1.156 | 1.061 | −8 | 1.077 | −7 |
| E | 1.161 | 0.990 | −15 | 1.120 | −4 |
| F | 1.142 | 1.000 | −12 | 0.946 | −17 |

TABLE 14c (all concentration expressed as %$^{w/w}$)

| | A | B | C* | D | E | F |
|---|---|---|---|---|---|---|
| Propylene Glycol | 46.88 | 46.88 | 23.45 | 15.9 | 25.3 | 24.8 |
| Dowicide 1 | 0.194 | 0.194 | 0.097 | 0.066 | 0.105 | 0.102 |
| Antifoam C | 0.052 | 0.052 | 0.026 | 0.017 | 0.028 | 0.027 |
| Peppermint Oil | 0.036 | 0.036 | 0.018 | 0.012 | 0.019 | 0.019 |
| FD&C Green Dye #1 | 0.0077 | 0.0077 | 0.0039 | 0.0026 | 0.0042 | 0.0041 |
| Makon 10 | 30.28 | 30.28 | 15.15 | 10.3 | 16.4 | 16.0 |
| Savinase ® 16.0 L | 2.67 | 2.67 | 1.33 | 0.90 | 1.44 | 1.41 |
| Alcalase ® 2.5 L | 21.38 | 21.38 | 10.70 | 7.23 | 11.5 | 11.3 |
| TEA | 14.82 | 7.39 | 0.00 | 0.00 | 0.00 | 0.00 |
| Tris | 0.00 | 0.00 | 6.01 | 2.85 | 5.82 | 5.65 |
| Boric Acid | 0.00 | 0.00 | 0.00 | 0.618 | 0.328 | 0.320 |
| Water | 34.91 | 84.42 | 43.64 | 30.0 | 47.2 | 45.8 |

*Formulation C is unstable

The results presented in Table 14b show that in comparison to the Tris buffer alone (solution C), a 2 M TEA buffer used alone (solution A) achieves maximum stability of enzymatic activity. The results also show that of the combination boric acid buffers evaluated, the combination of boric acid and Tris buffers in solutions D & E achieves maximum enzyme activity stability.

EXAMPLE 15

Effect of enzyme and Antifoam Agent on Blood-derived Foam

Table 15a compares foam volume versus reaction time of bovine blood with 7.5% $H_2O_2$ solutions at 23° C. The solution contained 40 ml of 7.5%$^{w/w}$ $H_2O_2$ (Degussa), 20 mg Antifoam C (Dow Corning), 200 mg Alcalase® 2.5 L and 0.8 ml whole bovine blood which were mixed in a 1 L Tripour beaker. Table 15b illustrates the relationship between foam volume and reaction time of bovine blood with 0.2% PAA/1.08% $H_2O_2$ solutions at 23° C. The solution contained 40 ml of 0.2% PAA/$H_2O_2$ (Degussa), 20 mg Antifoam C, 200 mg Savinase® 16.0 L and 0.8 ml bovine blood which were mixed in a 250 ml Tripour beaker. The pH of 7.5%$^{w/w}$ $H_2O_2$ and 0.2% PAA/$H_2O_2$ solutions were adjusted to 7.7 with 2 M Tris buffer prior to mixing with other ingredients. As a comparison, data for the mixed solution systems without enzymes and/or Antifoam C were also included. The foam volumes were measured immediately after the blood was added to the solutions. The formation of foam reflects the redox reaction between Fe(II) in the hemoglobin of the blood and $H_2O_2$ alone or $H_2O_2$/PAA and the catalytic degradation of $H_2O_2$ or $H_2O_2$/PAA by Fe(II) and Fe(III). One result of these reactions was released from the solutions in the form of gas bubbles which is likely $O_2$ gas. The bubbles when formed were immediately coated with bleached blood proteins to form foam. Tables 15a and b show that the foam is much less stable in the presence of enzymes, which implies that a considerable part of the blood protein molecules are hydrolyzed into small molecules by enzymes immediately after the blood was added to the solution. The results also show the utility of adding an antifoaming agent to the solution to reduce foam formation.

TABLE 15a

| | Foam Volume (ml) | | |
|---|---|---|---|
| Time (min) | 7.5%$^{w/w}$ H$_2$O$_2$ 2% Bovine blood | 7.5%$^{w/w}$ H$_2$O$_2$ 2% Bovine blood 0.5% Alcalase ® 2.5 L | 7.5%$^{w/w}$ H$_2$O$_2$ 2% Bovine blood 0.5% Alcalase ® 2.5 L 0.05% Antifoam C |
| 0 | 570 | 350 | 10 |
| 0.3 | | | 0 |
| 3 | | 150 | |
| 10 | | 50 | |
| 20 | 550 | 0 | |
| 120 | 250 | | |
| 1200 | 60 | | |

TABLE 15b

| | Foam Volume (ml) | | |
|---|---|---|---|
| Time (min) | 0.2% w/w PAA 1.08% w/w H$_2$O$_2$ 2% Bovine blood | 0.2% w/w PAA 1.08% w/w H$_2$O$_2$ 2% Bovine blood 0.5% Savinase ® 16.0 L | 0.2% w/w PAA 1.08% w/w H$_2$O$_2$ 2% Bovine blood 0.5% Savinase ® 16.0 L 0.05% Antifoam C |
| 0 | | | 0 |
| 1 | | 10 | |
| 3 | | 0 | |
| 7 | 140 | | |
| 15 | 120 | | |
| 90 | 10 | | |

EXAMPLE 16
Integrated Disinfection Regimen Soak Time Indicator

The enzymatic precleaner MetriZyme® (Metrex Research Corp.), which contains 10.94%$^{w/v}$ Alcalase® 2.5 L and 1.367%$^{w/v}$ Savinase® 16.0 L proteolytic enzymes and 0.004% FD&C blue dye #1, was mixed with 7.5%$^{w/v}$ H$_2$O$_2$ solution in a volume ratio of 1:128. The 7.5% H$_2$O$_2$ solutions at various pH were prepared by diluting 35%$^{w/w}$ H$_2$O$_2$ solution (Aldrich) and adjusting with 0.2 M Tris buffer. The initial colors of the MetriZyme/H$_2$O$_2$ mixed solutions were blue and faded with time. The color fading times measured with the naked eye for the MetriZyme®/H$_2$O$_2$ solutions at various pH are listed in Table 16.

TABLE 16

Relationship between color fading time and pH of the mixed solution of MetriZyme ®/7.5%$^{w/v}$ H$_2$O$_2$ (1:128 volume ratio) at room temperature.

| | Color fading time (min) | |
|---|---|---|
| pH | Start | Complete |
| 8.5 | 8 | 15 |
| 7.0 | 45 | 75 |
| 5.3 | Did not fade | NA |

MetriZyme® solution is blue when mixed with tap water in a 1:128 volumetric ratio. The disappearance of blue color over time in the MetriZyme®/H$_2$O$_2$ mixed solution suggests the occurrence of an oxidative bleaching reaction between H$_2$O$_2$ and dye. Surprisingly, such an oxidative reaction may not occur or can be too slow to be observed with the naked eye in a regular cleaning and disinfection time period of about 10 to 30 min if the solution pH is too low. It was also observed that at pH>8.5, the color of the mixed MetriZyme®/H$_2$O$_2$ solution can fade in less than 2 min, which is too short to be used as a solution soaking time indicator. Table 16 illustrates that the color fading time at pH 7–8.5 ranges between 8–15 and 45–75 min. These time ranges bracket the preferred 10–30 min soak times for high- or intermediate-level disinfection and enzymatic cleaning in the market. Thus, an H$_2$O$_2$ bleachable dye at a proper solution pH can be used as an integrated soak time indicator for simultaneous cleaning and disinfecting solutions containing at least H$_2$O$_2$ as one component of the disinfecting chemistry.

EXAMPLE 17
Kidney Dialyzer Cleaning Efficacy of H$_2$O$_2$/Enzyme Mixed Solution Three used kidney dialyzers obtained from a dialyzer reprocessing center were utilized for cleaning efficacy tests of a H$_2$O$_2$/enzyme mixed solution of the present invention. These dialyzers had been processed to the end of their useful life with a prior art reprocessing chemistry (Renalin® PAA solution without an enzyme). The blood chamber fiber bundle volumes of the used dialyzers were measured as follows: After both blood chamber and dialysate chamber of a dialyzer were filled with tap water, the dialyzer was tapped repeatedly to rid the chambers of air bubbles and all four outlets/inlets of the dialyzer were plugged to prevent water loss. The dialyzer was weighed before and after the water in the blood chamber was evacuated by blowing compressed air through it. The blood chamber (fiber bundle) volume was determined as the difference between the two weight values divided by the density of water. The used dialyzer initial volumes, $V_{used}$ (before treatment with the cleaning/disinfecting solution of the present invention), measured with the above method are consistent with the labeled minimum volumes (measured by the dialyzer processing center) which are about 80% of the new dialyzer volumes before the fiber bundles were clotted with patient blood. The cleaning/disinfecting solution in this example consisted of 128 parts of 7.5%$^{w/v}$ H$_2$O$_2$ and 1 part of Metrizyme® enzyme solution (Metrex Research Corp.) which contains 12%$^{w/v}$ Alcalase® 2.5 L+Savinase® 16.0 L combined. This solution has an initial proteolytic enzyme activity of 0.0031 A.U./ml. The pH of the mixed cleaning/disinfecting solution was adjusted to 8.5 with NaOH. Both blood and dialysate chambers of the dialyzers were then soaked with the above cleaning/disinfecting solution after the water in the dialysate chambers was removed. Multiple soaking intervals were utilized, with measurements of fiber bundle volume taken after each interval. The figure shows the relationship between the calculated percentage fiber bundle (blood chamber) volume recovery towards the 100% new dialyzer value and the cleaning/disinfecting solution soak time. The percentage fiber bundle volume recovery (P) was determined with the equation:

$$P = 400 \times \text{Fiber Volume Increase}/V_{used}$$

wherein V(new) is assumed to be 1.25×V(used), and % recovery P is also=(Vol. incr./(V(new)−V(used)))×100

As can be seen from the figure, from 60 to 90% of the clotted fiber bundle volume was recovered within 30 h of soaking with the cleaning/disinfecting solution of the present invention, which is well within the average Monday to Wednesday or Wednesday to Friday 43 h interdialysis interval. This example clearly indicates that the enzyme/H$_2$O$_2$ combined solution of the present invention can effectively remove the blood proteins and cellular debris clotted in the used dialyzer fiber bundles or alternatively, prevent blood proteins or debris from building up onto the dialyzer fiber bundle wall through regular treatment of the dialyzer following each dialysis procedure. Additionally, from the foregoing examples, it is expected that a solution comprising a proteolytic enzyme, $H_2O_2$ and PAA would be even more efficacious in cleaning a used dialyzer.

EXAMPLE 18
Simultaneous Enzymatic Cleaning and Disinfecting in One Step in Automated Instrument Disinfecting Systems The following powder formula in Table 18a was mixed with 92.5 g of 40° C. water. This mixture is equivalent to reprocessing chemistry compositions utilized in the Steris® System 1™ Sterile Processing System from the Steris Corporation. This mixture is known to produce a high-level disinfecting amount of PAA from the reaction between perborate and acetylsalicylic acid. The concentration of proteolytic enzyme in this example was initially about 0.02 A.U./ml. The temperature of the solution was kept at 40° C. using a temperature control bath. This temperature is essentially equivalent to the temperature used in the Steris® System 1™. During the mixing, 1.85 g of Azocasein was also added as a substrate for enzyme activity measurement (see the above in-situ protease activity assay method). At each time point listed in Table 18b, 5 ml of the above mixed solution was taken and mixed with 5 ml of 10%$^{w/v}$ TCA solution. The resulting precipitates of the TCA-containing solutions were removed using filtration after 15 min, and the absorbance of the supernatant was measured at 390 nm using a UV-visible spectrophotometer. As a control for the cleaning efficacy measurement, a mixed powder containing all the ingredients except Alcalase® 2.5 L was also mixed with Azocasein and water at 40° C.

TABLE 18a

| Ingredients | Grams |
| --- | --- |
| Sodium Perborate | 0.96 |
| Acetylsalicylic Acid | 2.31 |
| $Na_2HPO_4$ | 0.94 |
| $Na_3PO_4$ | 0.69 |
| Alcalase ® 2.5 L | 0.74 |

TABLE 18b

Absorbance (at 390 nm, normalized with dilution factors) of perborate/acetyl salicylic acid/enzyme mixed solution (see the above) at pH 6.6 at 40° C.

| Time since mixing | Without Alcalase ® 2.5 L | With Alcalase ® 2.5 L | Net Absorbance |
| --- | --- | --- | --- |
| 11 min | 0.526 | 7.740 | 7.214 |
| 40 min | 0.420 | 7.146 | 6.726 |
| 2.25 h | 0.901 | 7.233 | 6.332 |
| 7 h | 0.595 | 7.592 | 6.996 |

In this example, the Alcalase® 2.5 L-containing solution shows significant hydrolysis of Azocasein, indicating substantial cleaning activity, in the presence of the perborate/acetylsalicylic acid mixture. The hydrolysis of Azocasein has reached a maximum at or before the 11 min sampling time, indicating that the enzyme has been inactivated thereafter by exposure to the combination of PAA, 40° C. solution temperature and other excipients in the solution. Despite this subsequent inactivation, the very high enzyme activity observed over the first 11 min is representative of substantial cleaning activity. The currently marketed Steris® System 1™ utilizes a 12 min disinfection time, with the remainder of the total 30–35 min automated reprocessing time being allocated to the 4 following rinsing cycles and other automated processing cycles. Thus, the results of this example indicate that enzymatic cleaning can be simultaneously combined with disinfecting in one step in automated instrument disinfecting systems.

EXAMPLE 19
Tuberculocidal Effectiveness of Hydrogen Peroxide ($H_2O_2$)

A quantitative tuberculocidal test (suspension test) designed to determine the tuberculocidal effectiveness of a disinfectant/sterilant, following the EPA Guidelines for the Quantitative Tuberculocidal Procedure, was utilized.

Several $H_2O_2$ solutions were formulated without any additional preservative or other antimicrobial agents and without surfactants, chelators or organic buffers. The following formulas were tested, with $H_2O_2$ purchased from FMC Corp.:

| Formulation | Ingredient | Concentration (%$^{w/v}$) | pH |
| --- | --- | --- | --- |
| 1 | $H_2O_2$ | 6.0 | 8.5 |
|   | $Na_3HPO_4$ | 0.5 |   |
| 2 | $H_2O_2$ | 6.0 | 6.3 (adjusted with HCl) |
|   | $Na_3HPO_4$ | 0.5 |   |
| 3 | $H_2O_2$ | 6.0 | 5.0 (adjusted with HCl) |
|   | $Na_3HPO_4$ | 0.5 |   |

Two sterile glass test tubes to which an organic soil (2% bovine serum albumin) had been added, containing 18 ml of a particular test formula at 20° C., were each inoculated with 2 ml of a standardized suspension of *Mycobacterium bovis* (ATCC 35743) containing approximately $1.0 \times 10^6$ colony forming units (CFU)/ml. At contact times of 10 min for the formula at pH 6.3, and at 30 min for all formulas (pH 8.5, 6.3, 5.0), aliquots of the test suspension were removed and diluted in a neutralizer containing catalase to inactivate the $H_2O_2$. Serial tenfold dilutions of the neutralized suspension were then made in sterile saline. Each dilution was filtered through a 47 mm membrane filter with 0.45 micron porosity under a vacuum. Each filter was removed and aseptically placed on the surface of a Middlebrook 7H11 agar plate. The plates were incubated at 37° C.±2° C. for 15 to 25 days. Colonies were counted and the average CFU/ml was calculated for each contact time. The $\log_{10}$ reduction was determined by subtracting the $\log_{10}$ survivors at each contact time from the $\log_{10}$ at time zero CFU/ml.

Tuberculocidal activity test results.

| Formulation | pH | 0-Time CFU/mL | 10 min CFU/mL | 30 min CFU/mL |
| --- | --- | --- | --- | --- |
| 1 | 8.5 | $1.0 \times 10^6$ | NA | $3.5 \times 10^5$ |
|   | 8.5 | $1.0 \times 10^6$ | NA | $1.2 \times 10^5$ |
|   |   |   |   | Ave = $2.35 \times 10^5$ |
|   |   |   |   | $\log_{10}$ redn = 0.63 |
| 2 | 6.3 | $1.0 \times 10^6$ | $1.0 \times 10^6$ | $1.20 \times 10^5$ |
|   | 6.3 | $1.0 \times 10^6$ | $1.1 \times 10^6$ | $1.1 \times 10^6$ |
|   |   |   | Ave = $1.0 \times 10^6$ | Ave = $6.10 \times 10^5$ |
|   |   |   | $\log_{10}$ redn = 0.00 | $\log_{10}$ redn = 0.21 |
| 3 | 5.0 | $1.0 \times 10^6$ | NA | $1.0 \times 10^5$ |
|   |   | $1.0 \times 10^6$ | NA | $1.0 \times 10^5$ |
|   |   |   |   | Ave = $1.0 \times 10^5$ |
|   |   |   |   | $\log^{10}$ redn = 0.96 |

The tests indicate that $H_2O_2$ solutions alone, without any additional preservative or other antimicrobial agents, cannot achieve in a short time interval one of the fundamental antimicrobial efficacy requirements for a high- or intermediate-level disinfectant, namely tuberculocidal activity. The omission of the enzyme in this example is not significant, as the presence of the enzyme does not change the test result. The prior art compositions and methods (for example, U.S. Re. 32,672) do not disclose or teach tuberculocidal activity and high- or intermediate-level disinfection and sterilization.

Further evidence that hydrogen peroxide alone cannot achieve high- or intermediate-level disinfection is derived from experiments conducted with Sporox®, disclosed in Greene et al., U.S. Pat. Nos. 4,518,585 and 4,557,898. Sporox® product labeling states that the minimum effective hydrogen peroxide concentration for high-level disinfection is $6.0\%^{w/v}$. Greene '585 discloses one part aqueous acidic disinfecting and sterilizing compositions containing hydrogen peroxide, a surfactant, an organic or inorganic acid, an organic triazole corrosion inhibitor and an aqueous alcoholic mixture of a tertiary amine and a fatty acid alkanolamide such as linoleic diethanolamide. Suitable cationic surfactants include quaternary ammonium compounds such as alkyl dimethyl benzyl ammonium chloride and dialkyl quaternary ammonia compounds, which are known antimicrobial agents. Useful alcohols include the water-miscible alcohols such as isopropyl alcohol, also a known antimicrobial agent. Compositions of the invention have a pH below about 5, preferably about 3, and even more preferably about 1.8. An organic triazole corrosion inhibitor such as benzotriazole is thus disclosed to be necessary to prevent metal corrosion. Additionally, such one-part solutions are inherently unstable above pH 3, and even more so at pH 4–5 where metal corrosion is much less. Interestingly, in an attempt to understand the corrosive nature of Sporox®, the solution was tested for the presence of peracids using a recently developed sensitive HPLC assay for this purpose (Pinkernell et al., *Anal. Chem.*, 1997, 69:3623–3627). The assay is very sensitive, however, it is a general peracid detection assay and cannot determine specific peracids. This assay showed the presence of an unspecified peracid. It is believed this peracid in perlinoleic acid derived from the perhydrolysis of the amide bond in linoleic diethanolamide. Tuberculocidal activity tests were run according to the above procedure on Sporox® versus a pure solution of $6.0\%^{w/v}$ hydrogen peroxide at the same pH of 1.8 and containing only peroxide stabilizers present in the raw material. A concentration of $6.0\%^{w/v}$ hydrogen peroxide was selected, as this is the claimed minimum effective concentration of hydrogen peroxide for tuberculocidal activity and high-level disinfection in Sporox®. Another commercially available product, Cidex PA® was also tested. The results are shown in the following table:

| Compound | Recovery | Contact Time (min) | | | |
|---|---|---|---|---|---|
| | | 5 | 10 | 15 | 20 |
| 6% $H_2O_2$ pH 1.8 | CFU/ml | $7.4 \times 10^4$ | $4.1 \times 10^4$ | $2.7 \times 10^4$ | $3.4 \times 10^4$ |
| | % Reduction | 98.65 | 99.25 | 99.51 | 99.38 |
| | $\log_{10}$ Reduction | 1.87 | 2.13 | 2.31 | 2.21 |
| Cidex PA® | CFU/ml | $1.2 \times 10^4$ | $3.1 \times 10^3$ | $1.0 \times 10^1$ | $1.04 \times 10^1$ |
| | % Reduction | 99.78 | 99.94 | 100.0 | 100.0 |
| | $\log_{10}$ Reduction | 2.66 | 3.25 | 6.74 | 6.74 |
| Sporox® | CFU/ml | $1.0 \times 10^1$ | $1.0 \times 10^1$ | $1.0 \times 10^1$ | $1.0 \times 10^1$ |
| | % Reduction | 100.0 | 100.0 | 100.0 | 100.0 |
| | $\log_{10}$ Reduction | 6.74 | 6.74 | 6.74 | 6.74 |

These tests show in fact that while Sporox® kills 6.74 logs of *M. bovis* in 20 minutes, the $6.0\%^{w/v}$ solution of stabilized hydrogen peroxide kills only 2.21 logs in 20 minutes. Moreover, the amount of kill with the $6.0\%^{w/v}$ hydrogen peroxide solution does not increase with increasing time between 5 and 20 minutes. Thus, the tuberculocidal activity claim of Sporox®, which is based upon killing 6 logs in the specified regimen soak time of 30 minutes, is due to the presence of the peracid and perhaps other antimicrobial agents and cannot be achieved without it/them. These tests demonstrate again that hydrogen peroxide alone is not a high-level disinfectant.

An example of the compositions of the present invention which demonstrates tuberculocidal activity follows.

EXAMPLE 20

Tuberculocidal Tests of $H_2O_2$ Plus Peracetic Acid Solutions

Several $H_2O_2$ plus peracetic acid solutions were formulated and their tuberculocidal effectiveness was evaluated with a quantitative tuberculocidal test (suspension test), as in the previous example.

| Ingredients %$^{w/v}$ | Formulation 1 | Formulation 2 | Formulation 3 | Formulation 4 |
|---|---|---|---|---|
| $H_2O_2$ | 5 | 5 | 5 | 5 |
| Peracetic Acid | 0.1 | 0.2 | 0.3 | 0.4 |
| Benzotriazole | 0.65 | 0.65 | 0.65 | 0.65 |
| Dequest | 0.5 | 0.5 | 0.5 | 0.5 |
| Acetic Acid | 0.8 | 0.8 | 0.8 | 0.8 |
| pH | 3 | 3 | 3 | 3 |

Tuberculocidal activity test results:

| Formulation | 0-Time CFU/mL | 10 min CFU/mL | 20 min CFU/mL | 30 min CFU/mL |
|---|---|---|---|---|
| 1 | $1.0 \times 10^6$ | 0.0 $\log_{10}$ redn = 6.0 | 0.0 $\log_{10}$ redn = 6.0 | 0.0 $\log_{10}$ redn = 6.0 |
| Formulation | 0-Time CFU/mL | 10 min CFU/mL | 15 min CFU/mL | 20 min CFU/mL |
| 2 | $1.0 \times 10^6$ | 0.0 $\log_{10}$ redn = 6.0 | 0.0 $\log_{10}$ redn = 6.0 | 0.0 $\log_{10}$ redn = 6.0 |
| 3 | $1.0 \times 10^6$ | 0.0 $\log_{10}$ redn = 6.0 | 0.0 $\log_{10}$ redn = 6.0 | 0.0 $\log_{10}$ redn = 6.0 |
| 4 | $1.0 \times 10^6$ | 0.0 $\log_{10}$ redn = 6.0 | 0.0 $\log_{10}$ redn = 6.0 | 0.0 $\log_{10}$ redn = 6.0 |

The tuberculocidal activity test results show that all of the solutions, representing compositions of the present invention, tested at all time intervals exhibited maximum tuberculocidal activity, with a 6 $\log_{10}$ reduction, or total kill, of the entire initial inoculum challenge. Again, the omission of the enzyme in this example is not significant as the presence of the enzyme and its associated pH do not materially change the test result.

An example of a $H_2O_2$-containing solution of the present invention which does not contain peracetic acid and which also meets the tuberculocidal standards of high-level disinfection is disclosed in U.S. Pat. No. 4,518,585, which has previously been expressly incorporated herein by reference in its entirety.

It should be understood that the simultaneous cleaning and decontaminating compositions and methods of the present invention shown and described in the specification are only preferred embodiments of the inventors who are skilled in the art and are not limiting in any way. Various changes, modifications or alterations to these embodiments may be made or resorted to without departing from the spirit of the invention and the scope of the following claims.

What is claimed is:

1. A method for simultaneously cleaning and decontaminating a kidney dialyzer comprising contacting said dialyzer with a solution that simultaneously cleans and decontaminates said dialyzer, said solution comprising a mixture of $H_2O_2$ at about $0.5-1.5\%^{w/w}$ and PAA at about $0.05-3.0\%^{w/w}$ and human pepsin at about 0.00001–0.10 A.U./ml and having a pH between 1–6.

2. A composition for simultaneously cleaning and decontaminating a kidney dialyzer comprising a mixture of $H_2O_2$ at about $0.5-1.5\%^{w/w}$ and PAA at about $0.05-3.0\%^{w/w}$ and human pepsin at about 0.00001–0.10 A.U./ml and having a pH between 1–6.

3. A method for simultaneously cleaning and decontaminating a kidney dialyzer comprising contacting said dialyzer with a solution that simultaneously cleans and decontaminates said dialyzer, said solution comprising a mixture of $H_2O_2$ at about $0.5-1.5\%^{w/w}$ and PAA at about $0.05-3.0\%^{w/w}$ and human trypsin at about 0.00001–0.10 A.U./ml and having a pH between 6–9.

4. A composition for simultaneously cleaning and decontaminating a kidney dialyzer comprising a mixture of $H_2O_2$ at about $0.5-1.5\%^{w/w}$ and PAA at about $0.05-3.0\%^{w/w}$ and human trypsin at about 0.00001–0.10 A.U./ml and having a pH between 6–9.

* * * * *

UNITED STATES PATENT AND TRADEMARK OFFICE
CERTIFICATE OF CORRECTION

PATENT NO.      : 6,448,062 B1
DATED           : September 10, 2002
INVENTOR(S)     : Huth et al.

It is certified that error appears in the above-identified patent and that said Letters Patent is hereby corrected as shown below:

Title page,
Item [56], References Cited, OTHER PUBLICATIONS,
"M. Best" reference, reads "*Disinfactant*" and should read -- *Disinfectant* --; and
"Keay et al.," reference, reads "*Alkalilne*" and should read -- *Alkaline* --.

Column 2,
Line 50, reads "(Alcon, Inc.)." and should read -- (Alcon, Inc.)). --.

Column 4,
Line 21, reads "principle" and should read -- principal --.
Line 54, the sentence beginning with "When initially introduced" should start a new paragraph.

Column 8,
Line 47, reads "achieve cleaning: Additional" and should read -- achieve cleaning. Additional --.

Column 9,
Line 9, reads "does the it pertain to" and should read -- does it pertain to --.

Column 10,
Line 50, reads "enzymes are include" and should read -- enzymes include --.

Column 11,
Line 4, reads "device can rinsed" and should read -- device can be rinsed --.

Column 17,
Lines 18-19, reads "Termamy®" and should read -- Termamyl® --.

Column 21,
Line 32, reads "acid contant will" and should read -- acid content will --.
Line 36, reads "desireable" and should read -- desirable --.

Column 27,
Line 4, the sentence beginning with "Concentrations between about" should not begin a new paragraph.

Column 28,
Lines 10 and 11, reads "patent Nos" and should read -- patent Nos. --.

UNITED STATES PATENT AND TRADEMARK OFFICE
CERTIFICATE OF CORRECTION

PATENT NO. : 6,448,062 B1
DATED : September 10, 2002
INVENTOR(S) : Huth et al.

It is certified that error appears in the above-identified patent and that said Letters Patent is hereby corrected as shown below:

Column 29,
Line 30, reads "2.5.50.0" and should read -- 2.5-50.0 --.

Column 30,
Line 16, reads "Di-pac" and should read -- Di-Pac --.

Column 31,
Line 5, reads "20 min The" and should read -- 20 min. The --.
Line 27, reads "#06004" and should read -- #06004) --.

Column 32,
Line 15, reads "tablets the same" and should read -- tablets were the same --.

Column 34,
Lines 31 and 32, reads "7.5%$^{w/w}$" and should read -- 7.5% $^{w/v}$ --.

Column 35,
Line 55, Table 5b, the last two columns in the Table read:

| Azocasein Phosphate Buffer/ Neutrase ® | Absorbance Ratio of Neutrase ®/ solutions with and without 7.5% w/v $H_2O_2$ |
|---|---|
| 2.172 | 1.41 |
| 3.410 | 1.38 |
| 2.994 | 1.49 |
| 4.220 | 1.43 |

And should read

| 10 mM Phosphate Buffer/ Neutrase® | Absorbance Ratio of Neutrase®/ Azocasein solutions with and without 7.5% w/v $H_2O_2$ |
|---|---|
| 2.172 | 1.41 |
| 3.410 | 1.38 |
| 2.994 | 1.49 |
| 4.220 | 1.43 |

Column 36,
Line 18, Table 5c, reads "(25.6 $\mu$g/mL in" and should read -- (25.6 $\mu$g/mL) in --.

Column 37,
Line 33, reads "solutions 4" and should read -- solution 4 --.
Line 39, reads "principle" and should read -- principal --.

Column 39,
Line 18, reads "($H_3BO3$)" and should read -- ($H_3BO_3$) --.
Line 24, Table 7d, "$H_3BO_3$" should read -- $H_3BO_3$) --.

UNITED STATES PATENT AND TRADEMARK OFFICE
CERTIFICATE OF CORRECTION

PATENT NO. : 6,448,062 B1
DATED : September 10, 2002
INVENTOR(S) : Huth et al.

It is certified that error appears in the above-identified patent and that said Letters Patent is hereby corrected as shown below:

Column 41,
Line 29, Table 8, font is wrong reads "$^{PAA}$/Alcalase" and should read
-- PAA/Alcalase --.
Line 35, reads "demonstrate" and should read -- demonstrates --.

Column 41, lines 55, 56 and 66 and Column 42, lines 3, 7, 14, 18 and 20,
reads "Neutrase$^{TM}$" and should read -- Neutrase$^®$ --.

Column 46,
Line 43, reads "formulation are" and should read -- formulation) are --.
Line 43, reads "enzyme formulation are" and should read -- enzyme formulation) are --.

Column 50,
Line 39, reads "Metrizyme$^®$" and should read -- MetriZyme$^®$ --.
Line 58, there should be a period at the end of the sentence, after "100."
Line 64, reads "log$^{10}$" and should read -- log $_{10}$ --.

Column 52,
Lines 55-62, there should be more space between the "pH" column and the "0-Time CFU/mL" column so that there are two columns rather than it appearing to be only one column.

Column 53,
Line 43, reads "peracid in perlinoleic" and should read -- peracid is perlinoleic --.

Signed and Sealed this

Second Day of March, 2004

JON W. DUDAS
*Acting Director of the United States Patent and Trademark Office*